US011944271B2

(12) United States Patent
Sørensen et al.

(10) Patent No.: US 11,944,271 B2
(45) Date of Patent: Apr. 2, 2024

(54) ENDOSCOPE TIP PART WITH IMPROVED OPTICAL PROPERTIES

(71) Applicant: AMBU A/S, Ballerup (DK)

(72) Inventors: Morten Sørensen, Ballerup (DK); Hans Jochumsen, Allerød (DK)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 17/457,294

(22) Filed: Dec. 2, 2021

(65) Prior Publication Data

US 2022/0175226 A1 Jun. 9, 2022

(30) Foreign Application Priority Data

Dec. 8, 2020 (EP) ..................... 20212500

(51) Int. Cl.
*A61B 1/00* (2006.01)
*A61B 1/05* (2006.01)
*A61B 1/06* (2006.01)

(52) U.S. Cl.
CPC ...... *A61B 1/00135* (2013.01); *A61B 1/00009* (2013.01); *A61B 1/00043* (2013.01); *A61B 1/00066* (2013.01); *A61B 1/05* (2013.01); *A61B 1/0661* (2013.01)

(58) Field of Classification Search
CPC ............ A61B 1/00009; A61B 1/00096; A61B 1/00165; A61B 1/05; A61B 1/07; A61B 1/0011; A61B 1/00108; A61B 1/00105; A61B 1/00101; A61B 1/0661; G02B 23/2476
USPC ........................................ 600/104, 109, 129
See application file for complete search history.

(56) References Cited

U.S. PATENT DOCUMENTS

| 4,706,653 A | 11/1987 | Yamamoto |
| 4,753,224 A | 6/1988 | Tojo |
| 4,799,130 A | 1/1989 | Yabe |
| 4,805,596 A | 2/1989 | Hatori |

(Continued)

FOREIGN PATENT DOCUMENTS

| CN | 107174188 A | 9/2017 |
| DE | 29812048 U1 | 11/1998 |

(Continued)

OTHER PUBLICATIONS

Extended Search Report in related European Application No. 20212500. 1, dated Mar. 9, 2021, 7 pgs.

(Continued)

*Primary Examiner* — Ryan N Henderson
*Assistant Examiner* — Pamela F Wu
(74) *Attorney, Agent, or Firm* — Faegre Drinker Biddle & Reath LLP

(57) ABSTRACT

An endoscope tip part including a tip housing at least partially enclosing an interior cavity and including a window, and a vision assembly accommodated in the interior cavity and including an imaging subassembly including an image sensor viewing in an optical direction through the window of the tip housing, a light source comprising an illumination surface for emitting light, a separate frame component including a light shielding wall made of an opaque material and extending between the image sensor and the light source so as to at least partially shield the image sensor from light emitted from the light source.

18 Claims, 10 Drawing Sheets

(56) References Cited

U.S. PATENT DOCUMENTS

| | | | |
|---|---|---|---|
| 4,856,495 A | 8/1989 | Tohjoh et al. | |
| 4,860,732 A | 8/1989 | Hasegawa et al. | |
| 5,089,895 A | 2/1992 | Fraker et al. | |
| 5,193,525 A | 3/1993 | Silverstein et al. | |
| 5,193,526 A | 3/1993 | Daikuzono | |
| 5,305,736 A | 4/1994 | Ito | |
| 5,325,845 A | 7/1994 | Adair | |
| 5,379,756 A | 1/1995 | Pileski et al. | |
| 5,418,566 A | 5/1995 | Kameishi | |
| 5,419,311 A | 5/1995 | Yabe et al. | |
| 5,499,625 A | 3/1996 | Frass et al. | |
| 5,536,236 A | 7/1996 | Yabe et al. | |
| 5,562,602 A | 10/1996 | Yabe et al. | |
| 5,575,756 A | 11/1996 | Karasawa et al. | |
| 5,609,561 A | 3/1997 | Uehara et al. | |
| 5,685,823 A | 11/1997 | Ito et al. | |
| 5,688,221 A | 11/1997 | Yabe et al. | |
| 5,718,663 A | 2/1998 | Wulfsberg | |
| 5,725,476 A | 3/1998 | Yasui et al. | |
| 5,788,628 A | 8/1998 | Matsuno | |
| 5,836,869 A | 11/1998 | Kudo et al. | |
| 5,873,877 A | 2/1999 | McGaffigan | |
| 5,928,136 A | 7/1999 | Barry | |
| 5,993,378 A | 11/1999 | Lemelson | |
| 6,181,369 B1 | 1/2001 | Ooshima et al. | |
| 6,248,060 B1 | 6/2001 | Buess et al. | |
| 6,409,657 B1 | 6/2002 | Kawano | |
| 6,503,196 B1 | 1/2003 | Kehr et al. | |
| 6,533,722 B2 | 3/2003 | Nakashima | |
| 7,442,167 B2 | 10/2008 | Dunki-Jacobs et al. | |
| 7,662,093 B2 | 2/2010 | Gilad et al. | |
| 7,662,094 B2 | 2/2010 | Iddan | |
| 7,798,692 B2 | 9/2010 | Krupa et al. | |
| 8,189,062 B2 | 5/2012 | Irion et al. | |
| 8,414,480 B2 | 4/2013 | Kendale et al. | |
| 8,485,966 B2 | 7/2013 | Robertson | |
| 8,790,250 B2 | 7/2014 | Petersen et al. | |
| 8,870,753 B2 | 10/2014 | Boulais et al. | |
| 8,928,746 B1 | 1/2015 | Stevrin et al. | |
| 8,948,560 B1 | 2/2015 | Wach | |
| 9,125,582 B2 | 9/2015 | Petersen | |
| 9,158,037 B2 | 10/2015 | Otsuka | |
| 9,220,400 B2 | 12/2015 | Petersen | |
| 9,320,419 B2 | 4/2016 | Kirma et al. | |
| 9,521,942 B2 | 12/2016 | Robertson | |
| 9,615,730 B2 | 4/2017 | Pascal et al. | |
| 9,622,649 B2 | 4/2017 | Lin | |
| 9,633,649 B2 | 4/2017 | Lin | |
| 9,661,998 B2 | 5/2017 | Yoshino | |
| 9,814,374 B2 | 11/2017 | Kirma et al. | |
| 9,854,962 B2 | 1/2018 | McGrail et al. | |
| 10,245,402 B2 | 4/2019 | Daher et al. | |
| 10,321,804 B2 | 6/2019 | Jacobsen et al. | |
| 10,406,309 B2 | 9/2019 | Daher | |
| 10,835,103 B2 | 11/2020 | Tamura et al. | |
| 2002/0193663 A1 | 12/2002 | Matsuura | |
| 2003/0227547 A1 | 12/2003 | Iddan | |
| 2004/0027459 A1 | 2/2004 | Segawa et al. | |
| 2004/0064018 A1 | 4/2004 | Dunki-Jacobs et al. | |
| 2004/0199052 A1 | 10/2004 | Banik et al. | |
| 2004/0242963 A1 | 12/2004 | Matsumoto et al. | |
| 2005/0203341 A1 | 9/2005 | Welker et al. | |
| 2007/0249907 A1 | 10/2007 | Boulais | |
| 2008/0055403 A1* | 3/2008 | Salman | A61B 1/05 348/76 |
| 2008/0132760 A1 | 6/2008 | Takeuchi | |
| 2008/0188715 A1 | 8/2008 | Fujimoto | |
| 2008/0200764 A1 | 8/2008 | Okada | |
| 2008/0228035 A1 | 9/2008 | Hagihara et al. | |
| 2008/0242935 A1 | 10/2008 | Inoue | |
| 2008/0266441 A1 | 10/2008 | Ichimura | |
| 2009/0012358 A1 | 1/2009 | Ichihashi et al. | |
| 2009/0054728 A1 | 2/2009 | Trusty | |
| 2009/0177040 A1 | 7/2009 | Lyons et al. | |
| 2009/0209819 A1 | 8/2009 | Kitagawa et al. | |
| 2009/0227998 A1 | 9/2009 | Aljuri | |
| 2009/0253964 A1 | 10/2009 | Miyamoto | |
| 2009/0292168 A1 | 11/2009 | Farr | |
| 2010/0217082 A1 | 8/2010 | Ito et al. | |
| 2011/0118549 A1 | 5/2011 | Han | |
| 2011/0245617 A1 | 10/2011 | Kitano | |
| 2011/0288372 A1 | 11/2011 | Petersen | |
| 2011/0295072 A1* | 12/2011 | Boulais | A61B 1/051 600/176 |
| 2012/0041268 A1 | 2/2012 | Grey et al. | |
| 2012/0041534 A1 | 2/2012 | Clerc | |
| 2012/0172664 A1 | 7/2012 | Hayman | |
| 2012/0259173 A1 | 10/2012 | Waldron et al. | |
| 2012/0323078 A1 | 12/2012 | Kikumori et al. | |
| 2013/0035546 A1 | 2/2013 | Lin | |
| 2013/0175720 A1 | 7/2013 | Otsuka et al. | |
| 2013/0271588 A1 | 10/2013 | Kirma et al. | |
| 2014/0073853 A1 | 3/2014 | Swisher et al. | |
| 2014/0081085 A1 | 3/2014 | Takato et al. | |
| 2014/0150782 A1 | 6/2014 | Vazales et al. | |
| 2014/0313766 A1 | 10/2014 | Krupa et al. | |
| 2014/0328047 A1 | 11/2014 | Kamee | |
| 2015/0005580 A1 | 1/2015 | Petersen | |
| 2015/0036146 A1 | 2/2015 | Staloff | |
| 2015/0335227 A1 | 11/2015 | Jacobsen et al. | |
| 2016/0029879 A1 | 2/2016 | Ishikawa | |
| 2016/0051222 A1 | 2/2016 | Imahashi | |
| 2016/0106306 A1 | 4/2016 | Furuta | |
| 2016/0278620 A1 | 9/2016 | Kawayoke | |
| 2016/0287060 A1 | 10/2016 | Usuda | |
| 2017/0108691 A1 | 4/2017 | Kitano | |
| 2017/0108692 A1 | 4/2017 | Kitano et al. | |
| 2017/0245734 A1 | 8/2017 | Kaneko | |
| 2017/0251914 A1 | 9/2017 | Kitano | |
| 2017/0307872 A1 | 10/2017 | Hatase et al. | |
| 2017/0325663 A1* | 11/2017 | Levy | A61B 1/0615 |
| 2018/0070803 A1* | 3/2018 | Mikami | A61B 1/00009 |
| 2018/0078120 A1 | 3/2018 | Poll et al. | |
| 2018/0084981 A1 | 3/2018 | Wang | |
| 2018/0132700 A1* | 5/2018 | Ouyang | A61B 1/0684 |
| 2018/0160886 A1 | 6/2018 | Govani et al. | |
| 2018/0310890 A1 | 11/2018 | Li | |
| 2018/0317756 A1 | 11/2018 | Unsai | |
| 2019/0033506 A1 | 1/2019 | Weber | |
| 2019/0089875 A1 | 3/2019 | Fan | |
| 2019/0175007 A1 | 6/2019 | Sørensen et al. | |
| 2019/0183325 A1 | 6/2019 | Troller et al. | |
| 2019/0227298 A1 | 7/2019 | Elmaanaoui | |
| 2019/0246027 A1 | 8/2019 | Kuhn et al. | |
| 2019/0282070 A1* | 9/2019 | Vilhelmsen | A61B 1/00096 |
| 2019/0282077 A1 | 9/2019 | Sørensen et al. | |
| 2019/0298161 A1 | 10/2019 | Jensen | |
| 2019/0313891 A1 | 10/2019 | Oka | |
| 2019/0350442 A1 | 11/2019 | Giessen | |
| 2019/0374092 A1 | 12/2019 | Wu | |
| 2020/0100662 A1 | 4/2020 | Jensen et al. | |
| 2020/0110256 A1 | 4/2020 | Altshuler | |
| 2020/0196434 A1 | 6/2020 | Kuo et al. | |
| 2020/0214543 A1 | 7/2020 | Ben-Arye | |
| 2020/0288953 A1 | 9/2020 | Sørensen et al. | |
| 2020/0305699 A1* | 10/2020 | Herriges | A61B 1/00087 |
| 2021/0022558 A1 | 1/2021 | Schultheis et al. | |
| 2021/0127955 A1 | 5/2021 | Sørensen et al. | |
| 2021/0282631 A1 | 9/2021 | Schultheis et al. | |
| 2021/0338062 A1 | 11/2021 | Do | |
| 2022/0061645 A1 | 3/2022 | Jochumsen et al. | |

FOREIGN PATENT DOCUMENTS

| | | |
|---|---|---|
| DE | 10 2017 107 755 | 8/2018 |
| DE | 10 2018 102 587 | 1/2019 |
| DE | 102018107523 A1 | 10/2019 |
| DE | 10 2018 126 794 | 4/2020 |
| EP | 0 677 272 | 10/1995 |
| EP | 0756845 A1 | 2/1997 |
| EP | 0941691 A1 | 9/1999 |
| EP | 1494574 B1 | 2/2012 |
| EP | 1971888 B1 | 8/2017 |
| EP | 3539446 A1 | 9/2019 |

(56) References Cited

FOREIGN PATENT DOCUMENTS

| | | |
|---|---|---|
| EP | 3539447 A1 | 9/2019 |
| EP | 3539449 A1 | 9/2019 |
| JP | H 03264037 | 11/1991 |
| JP | 2004-016455 A | 1/2004 |
| JP | 2004-029235 A | 1/2004 |
| JP | 2005-304812 A | 11/2005 |
| JP | 3764512 B2 | 4/2006 |
| JP | 2009-125528 | 6/2009 |
| JP | 2009125528 A * | 6/2009 |
| JP | 2010169802 | 8/2010 |
| JP | 4914638 B2 | 4/2012 |
| JP | 2013009896 | 1/2013 |
| JP | 5503965 B2 | 5/2014 |
| JP | 2018015250 | 2/2018 |
| WO | WO 2005/023099 | 3/2005 |
| WO | WO 2008/115575 | 9/2008 |
| WO | WO 2010/066789 | 6/2010 |
| WO | WO 2010/066790 | 6/2010 |
| WO | WO 2010/129324 | 11/2010 |
| WO | 2012/077116 A1 | 6/2012 |
| WO | 2012/077117 A1 | 6/2012 |
| WO | WO 2014/106511 | 7/2014 |
| WO | WO-2014188787 A1 * | 11/2014 ......... A61B 1/00096 |
| WO | WO 2015/056106 | 5/2015 |
| WO | WO 2016/188537 | 12/2016 |
| WO | WO 2016/188541 | 12/2016 |
| WO | WO 2017/104048 | 6/2017 |
| WO | 2018/042715 A1 | 3/2018 |
| WO | WO 2018/059643 | 4/2018 |
| WO | 2019/049159 A1 | 3/2019 |
| WO | 2019/087178 A1 | 5/2019 |

OTHER PUBLICATIONS

European Search Report and Search Opinion Received for EP Application No. 20194137.4, dated Feb. 15, 2021, 11 pages.

* cited by examiner

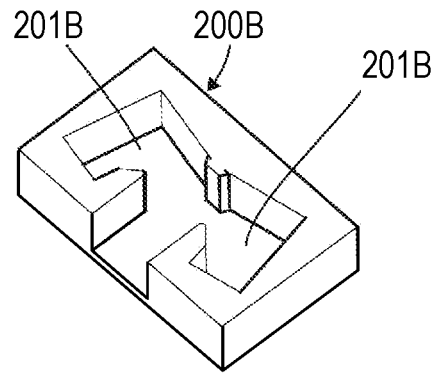
Figure 9A
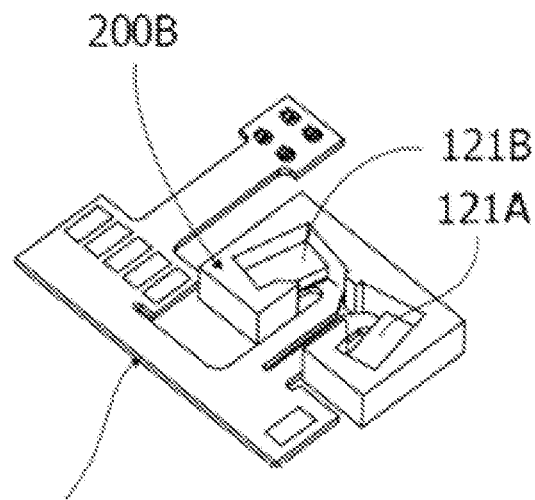
Figure 9B
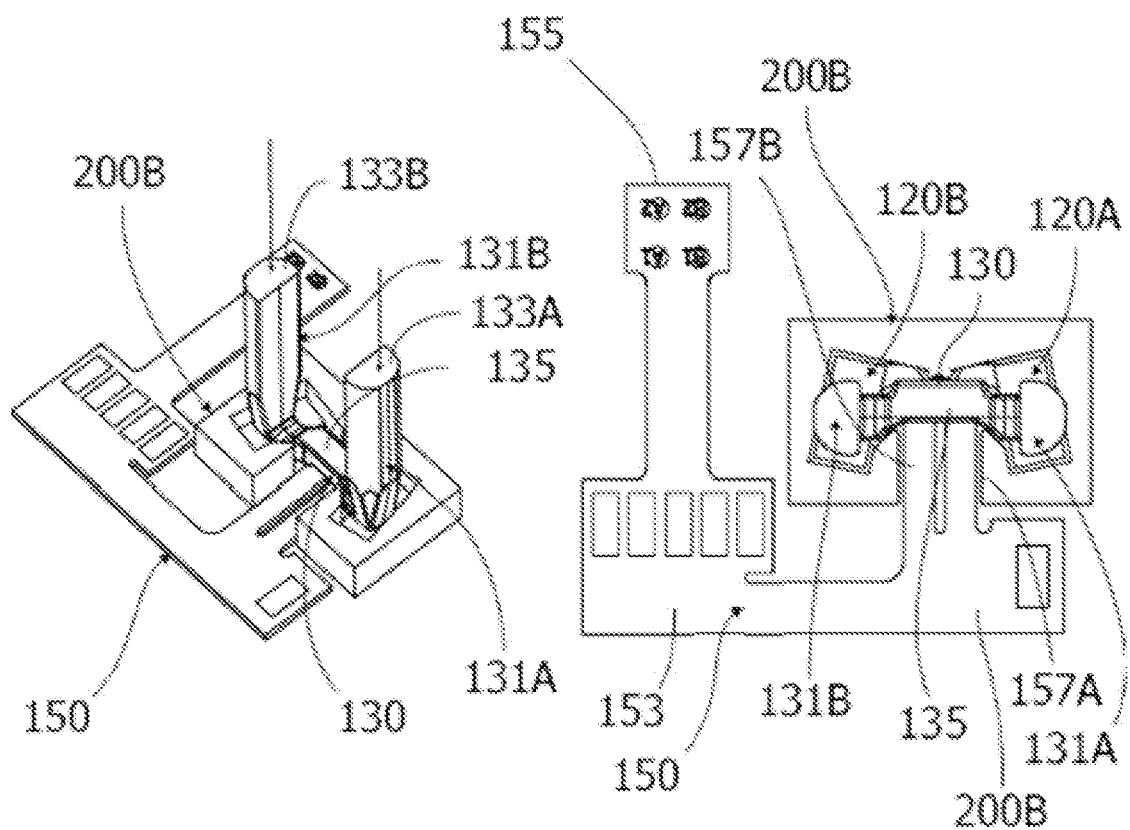
Figure 9C
Figure 9D

ENDOSCOPE TIP PART WITH IMPROVED OPTICAL PROPERTIES

CROSS-REFERENCE TO RELATED APPLICATIONS

This Application Claims Priority from and the Benefit of European Patent Application No. EP20212500.1, Filed Dec. 8, 2020, which is Incorporated Herein by reference in its entirety

TECHNICAL FIELD

The present disclosure relates to an endoscope tip part and a method for manufacturing such an endoscope tip part.

BACKGROUND

Insertion endoscopes are well-known devices in the medical field for visually examining the interior of a hollow organ or cavity of a body, such as lungs, by means of inserting an insertion portion of the endoscope. The insertion portion of the endoscope comprises an elongated insertion cord, a tip part, and a bending section connecting the insertion cord with the tip part. The endoscope typically has a handle connected to the insertion cord and positioned at the proximal end of the endoscope as seen from the operator. The endoscope further has an imaging subassembly with an image sensor arranged in the tip part at the distal end of the endoscope.

This definition of proximal as being closest to an operator and distal as being furthest from an operator is used throughout this disclosure. Illumination of the area in front of the distal tip of the endoscope is normally required, in particular in the field of vision of the image sensor. One known way of achieving such illumination is to incorporate one or more light sources, such as Light-emitting Diodes (LEDs), and one or more light guides in the tip part of the endoscope, e.g. as mentioned in commonly owned U.S. Patent Publication No. 2021/0127955 disclosing a disposable endoscope.

The bending section is provided in order to manoeuvre the endoscope inside the body cavity. The bending section has increased flexibility, e.g. achieved by a number of articulated segments of which the tip part forms the distalmost segment. Bending or straightening of the bending section in the insertion part of the endoscope is typically done by tensioning or slacking, respectively, steering wires running from the tip part through the remainder of articulated segments and along the inside of the elongated insertion cord to a control mechanism, such as a control lever, of the handle.

Data and/or power cables for the image sensor and other electronics, such as LED lighting accommodated in the tip part at the distal end of the endoscope, run along the inside of the elongated insertion cord and the bending section from the handle to the tip part. Furthermore, a working channel may run along the inside of the insertion cord and the bending section from the handle to the tip part, e.g. allowing liquid to be removed from the body cavity or allowing the insertion of medical tools or surgical instruments into the body cavity.

An ongoing goal in the field is to improve the optical performance of the endoscope tip part. In particular, there is a need for reducing or preventing light emitted from the light sources from entering the image sensor without being reflected back from the object to be visualised. Such light creates artifacts in the image produced by the image sensor and may also be known as stray light.

SUMMARY

On this background, it may be seen as an object of the present disclosure to provide an endoscope tip part with improved optical performance. In particular, by reducing the amount or eliminating stray light entering the image sensor.

Another object of the present disclosure is to provide a method of manufacturing such an endoscope tip part which reduces the variance in the optical properties of the imaging sensor and light source.

One or more of these objects may be met by aspects of the present disclosure as described in the following.

A first aspect of this disclosure relates to a tip part for a medical device, preferably an endoscope for visually inspecting inaccessible places, such as human body cavities, the endoscope tip part extending along a longitudinal axis from a proximal end thereof to a distal end thereof and comprising:

a tip housing forming an exterior surface of the endoscope tip part and at least partially enclosing a fluid-sealed interior cavity, the interior cavity preferably being gas-filled, e.g. air-filled, the tip housing preferably having a distal end forming the distal end of the endoscope tip part, the tip housing including:
  a side wall extending circumferentially around and longitudinally along the longitudinal axis and preferably having a proximal opening at the proximal end of the endoscope tip part providing access to the interior cavity; and
  a window having an interior window surface facing the interior cavity of the tip housing, the window preferably being positioned at the distal end of the endoscope tip part; and
a vision assembly accommodated in the interior cavity of the tip housing and including:
  an imaging subassembly comprising an image sensor viewing in an optical direction preferably through the window of the tip housing;
  one or more light sources, such as a light-emitting diode or an optical fibre, each light source comprising an illumination surface from which the light source is configured to emit light in an illumination direction;
  preferably a light guide part comprising at least one light guide, each light guide having a light entry surface and a light exit surface and being configured for receiving light from at least one respective light source of the one or more light sources through its light entry surface and propagating said light through to its light exit surface and out through the window of the tip housing;
  preferably an electrical circuit comprising an imaging circuit portion, the imaging circuit portion being in electrical communication with the image sensor, the electrical circuit being configured for transmitting an image signal generated by the image sensor indicative of the view in the optical direction; and
  a frame component being formed, preferably monolithically, as a separate component, the frame component supporting and fixing the imaging subassembly, the one or more light sources, and preferably the electrical circuit, relative to each other,
wherein the frame component comprises a light shielding wall being made of an opaque material and extending, preferably longitudinally and circumferentially relative to the optical direction at least partially around the imaging subassembly, between the image sensor and the one or more light sources, in particular the illumination surfaces of the one or more light sources, and/or light guides so as to at least partially shield the image sensor from light emitted from the one or more light sources.

By providing the frame component with a light shielding wall stray light from the light source(s) can be reduced or even prevented from entering the image sensor from the proximal half of the imaging subassembly. Furthermore, the light shielding wall may protect the imaging subassembly of the vision assembly, in particular the attachment between the imaging circuit portion and the frame component, prior to assembly with the tip housing.

Additionally or alternatively, the imaging subassembly may comprise one or more lenses arranged in front of the image sensor so that the optical direction extends through the one or more lenses. The one or more lenses may be arranged in a lens barrel fixing the relative position of the one or more lenses and preferably the image sensor. The lens barrel may preferably be opaque to provide optical shielding for the one or more lenses.

Additionally or alternatively, the light guide part may comprise a light guide for each light source.

Additionally or alternatively, the illumination surface of each of the one or more light sources may be arranged proximally relative to the image sensor, preferably so that the respective illumination direction passes by a side of the image sensor, and the light shielding wall may comprise an end wall extending transversely to the optical direction, the end wall extending between the image sensor and the one or more light sources so as to optically shield a proximal side of the image sensor from the one or more light sources.

Additionally or alternatively, the illumination direction(s) may preferably extend in parallel or substantially parallel to the optical direction.

In this arrangement, the end wall may prevent stray light emitted from the one or more light sources from entering behind the image sensor. The end wall thereby forms a light shield for the imaging subassembly, thus improves the quality of the image sensor.

Additionally or alternatively, the light shielding wall of the frame component may comprise one or more side walls for each light guide extending along the respective light guide and being arranged between the light guide and the imaging subassembly. The one or more side walls may be U-shaped along the longitudinal direction.

By such an arrangement of the side wall(s) of the light shielding wall, the side wall(s) prevent(s) stray light emitted from the one or more light sources or escaping from the light guides from entering the image sensor thereby forming an light shield for the imaging subassembly.

Additionally or alternatively, the one or more side walls may extend longitudinally along the longitudinal axis from the end wall.

Additionally or alternatively, the light guide part may be formed, preferably monolithically, as a separate component, and the illumination surface of each of the one or more light sources may be attached, preferably adhered, to the light entry surface of its respective light guide.

Additionally or alternatively, the frame component may comprise an imaging attachment surface, and the imaging circuit portion may be attached, preferably adhered, to the imaging attachment surface.

Additionally or alternatively, the upper section of the main circuit portion may be connected to the imaging circuit portion via an imaging connecting circuit portion supported by an imaging connecting surface of the frame component.

Additionally or alternatively, the imaging attachment surface may comprise a protrusion protruding from the imaging attachment surface and may be in direct contact with the imaging circuit portion. The protrusion may aid in ensuring a correct orientation of the imaging subassembly, specifically the optical direction, relative to the frame component. The adhesive may surround the protrusion and fix the imaging subassembly via the imaging circuit portion to the imaging attachment surface.

Additionally or alternatively, the electric circuit may comprise a main circuit portion being in electrical communication with the imaging circuit portion and preferably the illumination circuit portion(s), and the main circuit portion having a bend arranged around the frame component.

Additionally or alternatively, the main circuit portion interconnects various electronic components, e.g. capacitors, transistors, cables, and the like, of the electrical circuit.

Additionally or alternatively, the frame component may comprise an upper supporting surface and a lower supporting surface arranged opposite of the upper supporting surface, the upper supporting surface and lower supporting surface may be connected by an intermediate connecting surface. The upper supporting surface, lower supporting surface, and intermediate connecting surface may be positioned between the proximal collar and the intermediate collar. The upper supporting surface may support or fix, e.g. by adhesion, an upper section of the main circuit portion. The lower supporting surface may support or fix, e.g. by adhesion, a lower section of the main circuit portion. The intermediate connecting surface of the frame component may support the bend of the main circuit portion which connects the upper section of the main circuit portion with the lower section of the main circuit portion so that the main circuit portion is folded around the frame component.

Additionally or alternatively, the endoscope tip part may comprise a plurality of data and/or electrical cables attached to the upper section of the main circuit portion, e.g. via soldering. The plurality of cables may be configured for transmitting electrical signals between the electrical circuit and a handle of the endoscope. The frame component may comprise a cut-out configured for accommodating the plurality of cables in a proximal end thereof. The cut-out may improve manufacturing as the plurality of cables can be laid to extend along the longitudinal axis and then be attached to the electrical circuit.

Additionally or alternatively, the electrical circuit may comprise an illumination circuit portions for each light source, each illumination circuit portion being in electrical communication with a respective light source of the one or more light sources, each illumination circuit portion being electrically connected to the main circuit portion by a respective bridge circuit portion of the electrical circuit preferably having a wave-shaped extent along the optical direction.

Such a wave shaped bridge circuit allows the respective light source to be moved axially relative to the longitudinal axis relative to the remaining parts of the vision assembly prior to fixing thereby allowing adjustment to absorb axial production variance and thus ensure a greater optical performance, i.e. by reducing an axial gap between the window of the tip housing and the vision assembly relative to the longitudinal axis.

Additionally or alternatively, the one or more light sources may include at least a first light source and a second light source, and the electrical circuit may have a slit separating the bridge circuit portions associated with the first and second light sources.

By separating bridge circuit portions allows the assembler to flex the bridge portions to adjust the illumination circuit portions transversely to the longitudinal axis, thereby absorbing variance and thus ensuring greater optical performance, i.e. by providing a more consistent alignment between the one or more light sources and the light guide part.

Additionally or alternatively, the imaging circuit portion and/or the illumination circuit portion may be flexible so that, prior to assembly, the image sensor and light source(s) are movable relative to each other. This may be an advantage in assembly, as the image sensor and light source(s) can be moved relatively to their desired position.

Additionally or alternatively, the electrical circuit may be configured for transmitting the image signal to an external electrical component, such as a circuit, preferably positioned in the handle. The image signal may be transmitted from the electrical circuit of the endoscope tip part via a wired connection or a wireless connection. Thus, the electrical circuit does not necessarily comprise a cable extending between the endoscope tip part and the handle for transmitting the image signal.

Additionally or alternatively, the frame component comprises an illumination attachment surface for each light source, and each light source, preferably via the illumination circuit portion, may be attached, preferably adhered, to a respective illumination attachment surface.

Additionally or alternatively, the frame component may comprise a proximal collar having an outer contour corresponding to an interior surface of the circumferential wall of the tip housing. A gap between the proximal collar and the interior surface of the circumferential wall of the tip housing may be filled with a cured adhesive.

Additionally or alternatively, the frame component may comprise an intermediate collar corresponding to the interior surface of the circumferential wall of the tip housing. The light shielding wall may be arranged distally relative to the intermediate and/or the proximal collar.

Additionally or alternatively, the electrical circuit may be provided on a flexible circuit board (FPC).

Additionally or alternatively, the endoscope tip part may comprise a sealing component attached to a circumference of an interior surface of the tip housing so as to fluid-seal the interior cavity. The sealing element may further close the proximal opening of the tip housing.

Additionally, the sealing component may preferably be formed as a separate component or alternatively be formed as an integral part of the frame component.

Additionally or alternatively, the tip housing may comprise a distal working channel opening, a proximal working channel opening, and a working channel cavity extending between the distal working channel opening and the proximal working channel opening. The working channel cavity may be separated from the interior cavity of the tip housing by a working channel wall and may be configured for insertion of medical tools or surgical instruments therethrough.

Additionally or alternatively, the working channel cavity may have a substantially circular or oval cross-section relative to the longitudinal axis. A cross-section of interior cavity of the tip housing relative to the longitudinal axis may have a substantially crescent shape so that the circumference of the exterior housing surface of the tip housing is substantially circular.

A second aspect of this disclosure relates to an endoscope for visually inspecting inaccessible places such as human body cavities, comprising:
   a handle for gripping by an operator and preferably comprising a control device;
   an endoscope tip part according to the first aspect of this disclosure;
   an insertion cord for insertion into a patient, the insertion cord extending from the handle to the endoscope tip part and comprising a bending section;
   one or more cables running through the insertion cord and electrically connecting the endoscope tip part, preferably the electrical circuit of the endoscope tip part, with the handle; and
   preferably at least one steering wire connecting the control device with a distal end of the bending section so that manipulation of the control device causes bending of the bending section.

A third aspect of this disclosure relates to an endoscope system for visually inspecting inaccessible places, such as human body cavities, the endoscope system comprising a monitor, and an endoscope according to the second aspect of this disclosure or an endoscope comprising an endoscope tip part according to the first aspect of this disclosure, wherein the endoscope is connectable to the monitor, and the monitor is configured for displaying an image captured by the image sensor of the endoscope tip part.

A fourth aspect of this disclosure relates to a method for assembling a vision assembly for an tip part for a medical device or preferably an endoscope, the tip part is preferably according to any one of the first aspect of this disclosure, the tip part extending along a longitudinal axis from a proximal end thereof to a distal end thereof, the method comprising the steps of:
   providing:
      an imaging subassembly comprising an image sensor viewing in an optical direction;
      one or more light sources, such as a light-emitting diode or an optical fibre, each light source comprising an illumination surface from which the light source is configured to emit light in an illumination direction;
      a light guide part comprising at least one light guide, each light guide having a light entry surface and a light exit surface and being configured for receiving light from at least one respective light source of the one or more light sources through its light entry surface and propagating said light out through its light exit surface;
      preferably an electrical circuit comprising a main circuit portion and an imaging circuit portion, the imaging circuit portion being in electrical communication with the image sensor, the electrical circuit being configured for transmitting an image signal generated by the image sensor indicative of the view in the optical direction;
      a frame component being formed, preferably monolithically, as a separate component; and
   preferably performing a first alignment sequence to obtain a first subassembly, the first alignment sequence comprises the steps of:
      preferably arranging the imaging subassembly and the frame component in a first jig;
      aligning the image sensor with the frame component by axially pushing against an axial stop, preferably of the first jig, and by transversely pushing against a transverse stop, preferably of the first jig; and fixing, e.g. by adhering, the imaging subassembly to the frame component, and preferably fixing, e.g. by adhering, the imaging circuit portion to the frame component; and/or preferably performing a second alignment sequence to obtain a second subassembly, the second alignment sequence comprises the steps of:
  preferably arranging one or more light sources and the light guide part in a second jig;
  aligning each at least one light source of the one or more light sources with the respective light guide of the light guide part by pushing against an axial stop, preferably of the second jig; and
  fixing, e.g. by adhering, each of the at least one light source of the one or more light sources to the light entry surface of the respective light guide; and/or preferably performing a third alignment sequence to obtain the vision assembly, the third alignment sequence comprises the steps of:
  preferably arranging the first subassembly and the second subassembly in a third jig;
  aligning the first subassembly and the second subassembly; and
  fixing, e.g. by adhering, the second subassembly to the frame component.

Additionally or alternatively, each light source may be arranged in a separate alignment hole of the second jig and the light guide part may be arranged in a guide of the second jig so as to align the relative position of the one or more light sources and the light guide component. The slit separating the bridge circuit portions may enable adjustment of the relative position of imaging circuit portions (and thus the light sources) by flexing the bridge circuit portions thereby allowing the imaging circuit portions to be arranged in the alignment holes of the second jig even if manufactured with relatively large tolerances.

Additionally or alternatively, the method of the fourth aspect may be used for assembling the endoscope tip part for an endoscope for visually inspecting inaccessible places, such as human body cavities, the method further comprising the steps of:
  providing a tip housing extending circumferentially around and longitudinally along the longitudinal axis and defining an exterior surface of the endoscope tip part, the tip housing at least partially enclosing an interior cavity and having a proximal opening at the proximal end of the endoscope tip part providing access to the interior cavity, the tip housing including a window having an exterior window surface facing the exterior of the endoscope tip part and an interior window surface facing the interior cavity of the tip housing; and
  inserting the vision assembly through the proximal opening of the tip housing so that the image sensor views through the window of the tip housing, and so that each light guide of the light guide part is arranged to propagate light received through its light entry surface through its light exit surface and out through the window of the tip housing; and
  sealing the proximal opening of the tip housing so that the interior cavity is fluid-sealed.

Additionally or alternatively, the step of inserting the vision assembly further involves contacting the light exit surfaces of the light guide component with the interior surface of the window and/or contacting a distal end of the imaging subassembly, e.g. a distal end of a lens barrel, with the interior surface of the window.

The present disclosure makes a distinction between optical fibres and light guides. Optical fibres in this context are to be understood as highly elongated and flexible elements, where the length is several orders of magnitude larger than the diameter, providing the fibres with a high degree for flexibility to allow them to conduct luminous flux to a desired place. Light guides are to be understood as much shorter, preferably rigid elements adapted to guide and distribute light in a desired manner. Furthermore, while optical fibres are used to transport light, as used herein light guides are primarily used to reshape the incoming light beam typically by varying the cross-section of the light guide along the length of the light guide.

A person skilled in the art will appreciate that any one or more of the above aspects of this disclosure and embodiments thereof may be combined with any one or more of the other aspects of this disclosure and embodiments thereof.

BRIEF DESCRIPTION OF THE DRAWINGS

Embodiments of this disclosure will be described in more detail in the following with regard to the accompanying figures. The figures show one way of implementing the present invention and are not to be construed as being limiting to other possible embodiments falling within the scope of the attached claim set.

FIGS. 9A-9D are schematic perspective illustrations of a second alignment sequence involving a second jig.

DETAILED DESCRIPTION OF THE INVENTION

Figure 1:
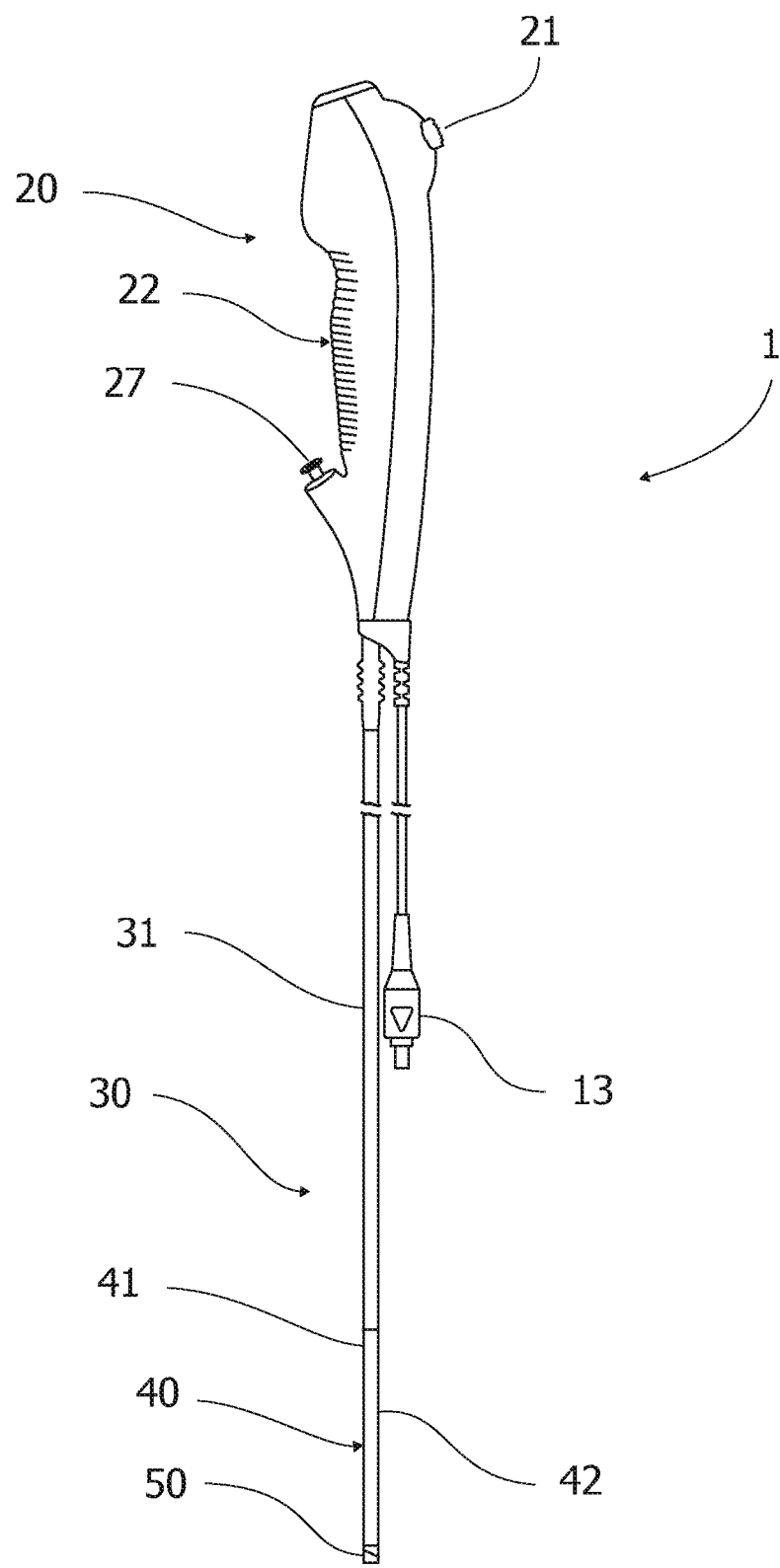
FIG. 1 is a schematic perspective illustration of an endoscope according to this disclosure.
Figure 3:
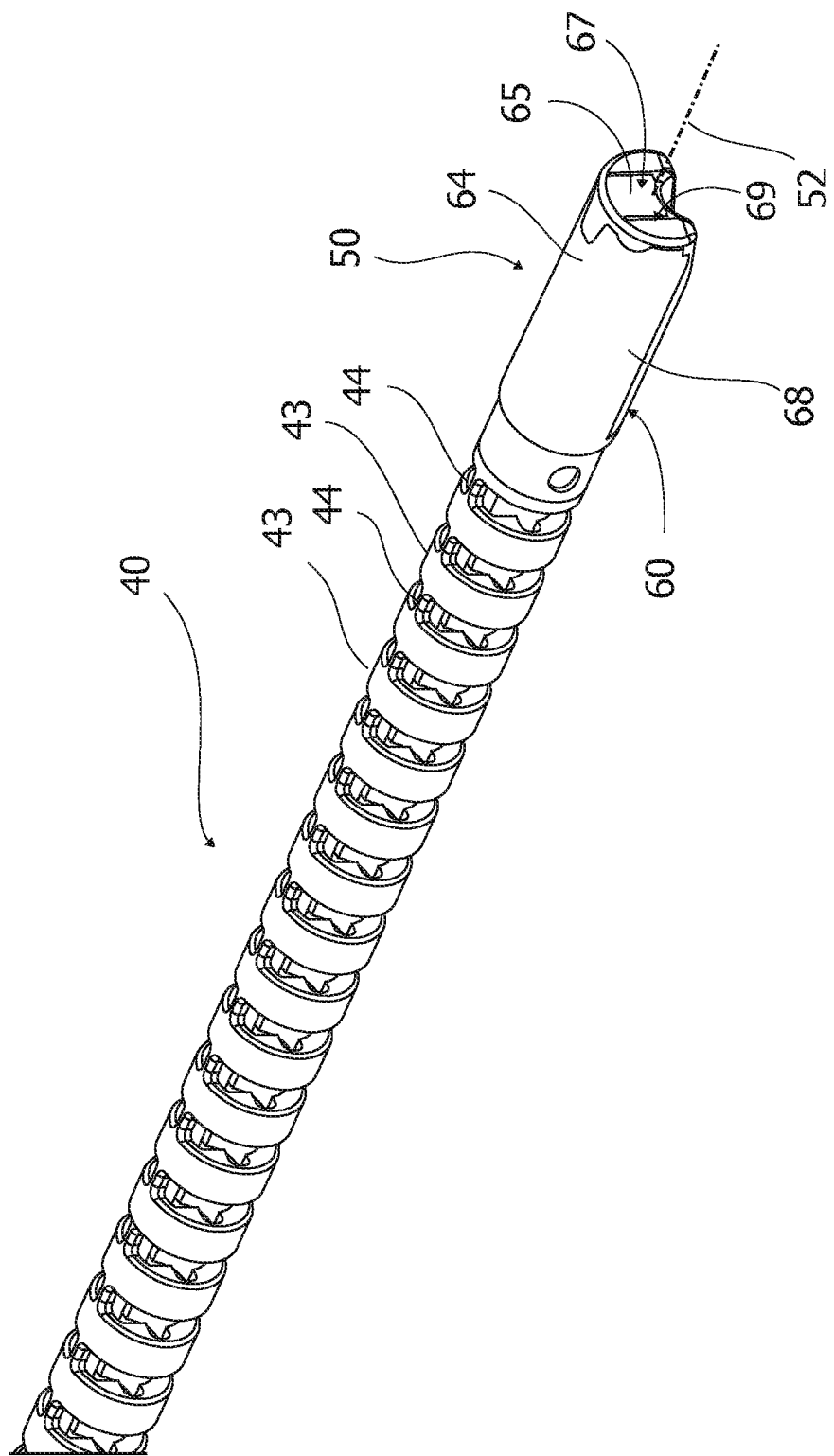
FIG. 3 is a schematic perspective illustration of a distal end of the endoscope shown in FIG. 1 showing an endoscope tip part of the endoscope in greater detail.

FIG. 1 illustrates an endoscope 1, which is disposable and not intended to be cleaned and reused. The endoscope 1 comprises a distal tip part 50, a handle 20 with a handle housing 22 for gripping and a control lever 21, an insertion cord 30, which may also be known as an insertion tube, for insertion into a patient and extending between the handle 20 and a proximal end 41 of a bending section 40, and a vision assembly 100 (best seen in FIGS. 4A-5A) positioned in the distal tip part 50. The vision assembly 100 is in signal communication with a circuit (not shown) of the handle 20 via data and power cables 159 (as best seen in FIGS. 4A-5A). The insertion cord 30 has an exterior tubular surface facing the surroundings of the endoscope 1. Furthermore, a working channel (not shown) run along the inside of the insertion cord 30 from a working channel opening 27 of the handle 20 to a distal tip working channel opening 72 of the distal tip part 50, which is best seen in FIGS. 5B-6B. The working channel allows liquid or air to be added to and/or removed from the body cavity or allows the insertion of medical tools or surgical instruments into the body cavity. The bending section 40 comprises articulated segments 43 and hinges 44 connecting the segments 43, which is best seen in FIG. 3. Two steering wires (not shown) run from the distal tip 50 to the control lever 21 of the handle 20. The control lever 21 can, upon manipulation, tension a respective steering wire to articulate the bending section 40, thereby allowing the operator to steer the distal tip 50 during endoscopy. The segments and hinges are covered by a thin outer sleeve 42, thereby providing an additional layer of sealing for the connection between the distal tip part 50 and the bending section 40. The thin outer sleeve 42 also provides a smooth outer surface for the bending section 40 to improve the comfort of a patient undergoing endoscopy.

Figure 2:
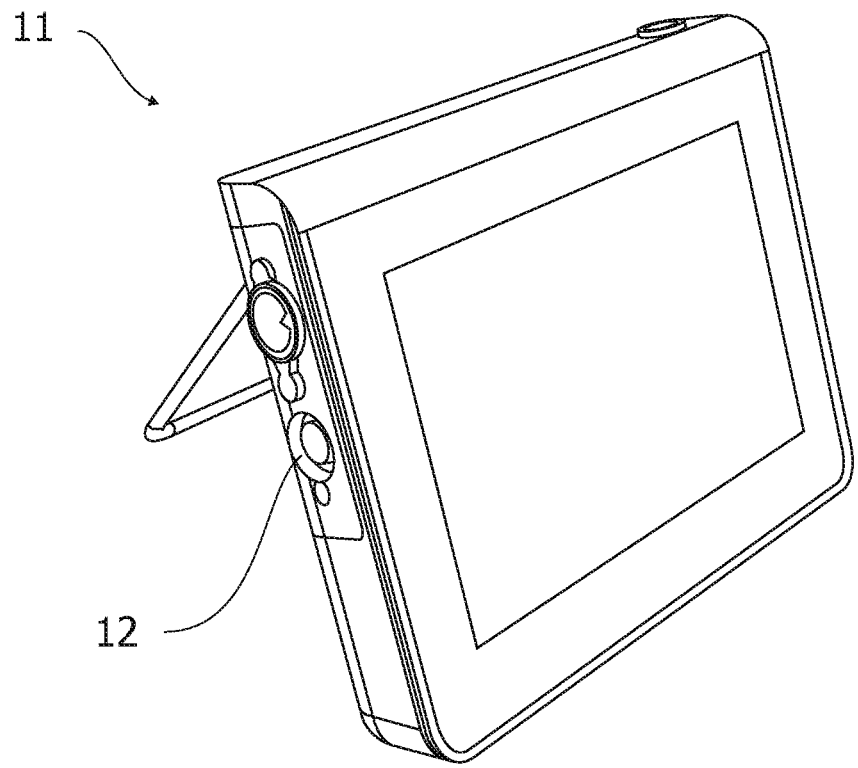
FIG. 2 is a schematic perspective illustration of a monitor connectable to the endoscope.

In FIG. 2, a monitor 11 is shown. The monitor 11 comprises a cable socket 12 to which a monitor cable 13 of the endoscope 1 (shown in FIG. 1) can be connected to establish signal communication between the vision assembly 100 (shown in FIGS. 4A-5A) of the endoscope 1 and the monitor 11 via the circuit. The monitor 11 display images and/or video captured by the camera of the endoscope 1 thus allowing an operator to "see" the body cavity through the camera of the endoscope 1.

Figure 5B:
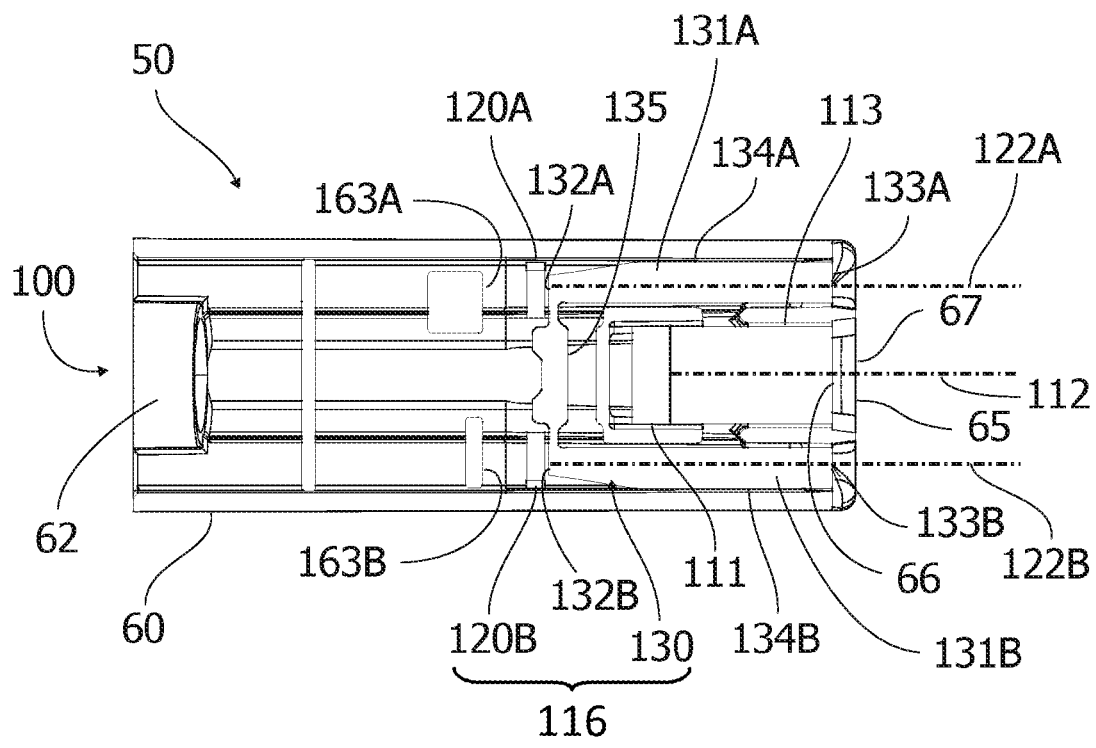
FIG. 5B is a schematic illustration of a cross-section along the longitudinal axis of the endoscope tip part and through light guides of the vision assembly.
Figure 6A:
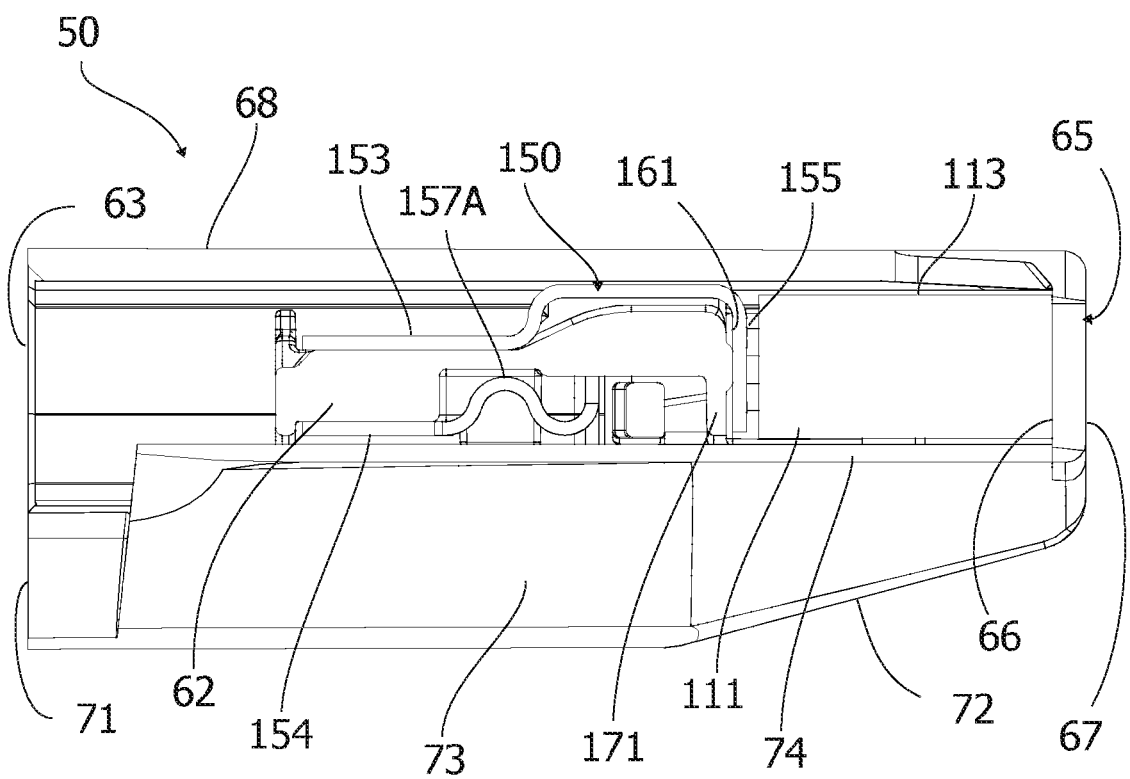
FIG. 6A is a schematic illustration of a cross-section along the longitudinal axis of the endoscope tip part and perpendicular to the cross-section of FIG. 5B.

Turning to FIG. 3, the endoscope tip part 50 can be seen in greater detail attached to the bending section 40 (the outer sleeve of the bending section 40 is omitted for visualisation purposes). The tip part 50 comprises a tip housing 60 having an exterior housing surface 64 defining the exterior surface of the tip part 50. The tip housing 60 comprises a cylindrical shell-shaped circumferential wall 68 extending circumferentially around a longitudinal axis 52 and surrounding an interior cavity 62, as best seen in FIGS. 5B and 6A. The circumferential wall 68 is closed at a distal end of the tip housing 60 by a distal end wall 69 and has a proximal opening 63 (as best seen in FIGS. 5B and 6A), which provides the only access to the interior cavity 62, at the opposite end of the tip housing 60. The tip housing 60 comprises an opaque portion and a transparent portion including a window 65 arranged in the distal end wall 69. The window 65 has an interior surface 66 (as best seen in FIGS. 5B and 6A) facing the sealed interior cavity 62 and an exterior window surface 67 forming part of the exterior surface 51 of the tip housing 60. The tip housing is preferably manufactured by two-shot injection moulding processes so that the transparent portion (including the window 65) is formed by a transparent polymer material shot of the two shot injection moulding process and the opaque portion is formed by an opaque polymer material shot of the two shot injection moulding process. Thus, the tip housing 60 is formed as a monolithic, i.e. single, polymer piece. The tip part 50 further comprises a separately formed sealing element (not shown) arranged in and sealing the proximal opening 63 via an adhesive, thereby fully liquid- and gas-sealing the air-filled interior cavity 62. The sealing element may be a polymer plug and an adhesive may fix and seal a gap between this plug and the interior surface of the tip part 50. The sealing element may further fixate the vision assembly by pushing the vision assembly axially along the longitudinal direction against the tip housing 60.

Figure 4A:
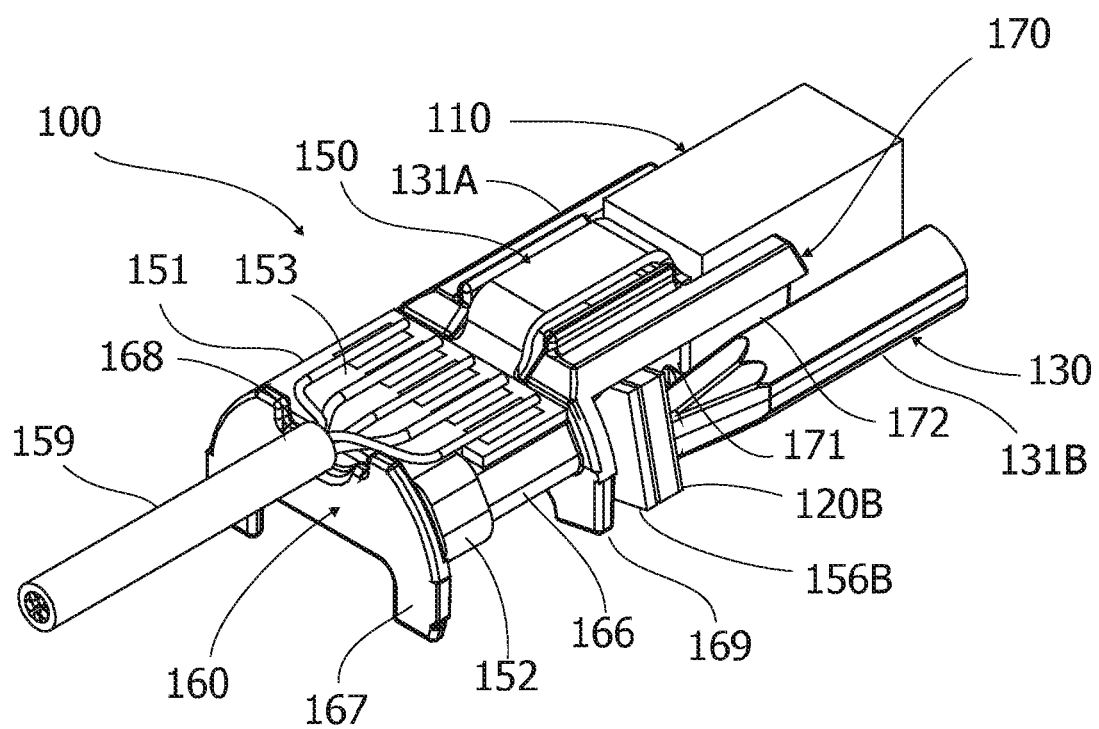
FIGS. 4A, 4B, and 5A are schematic perspective views of a vision assembly accommodated in the endoscope tip part shown in FIG. 3 from a proximal, distal, and lower direction, respectively.
Figure 4B:
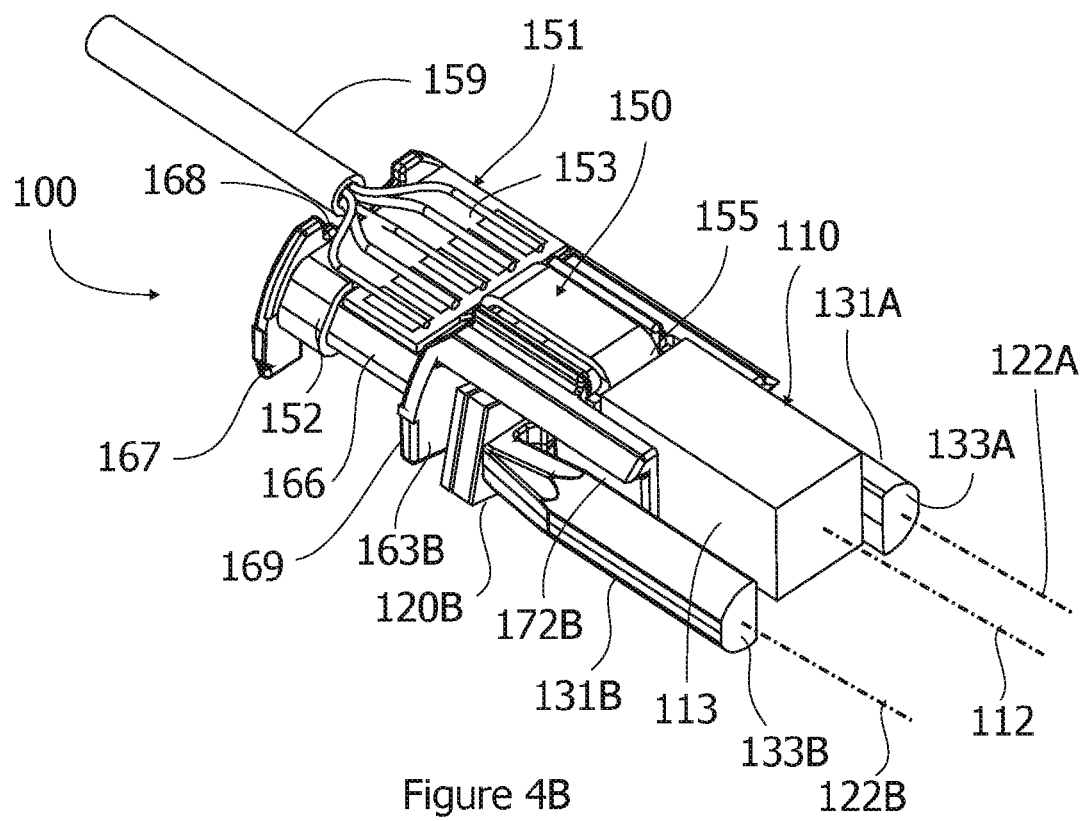
Figure 5A:
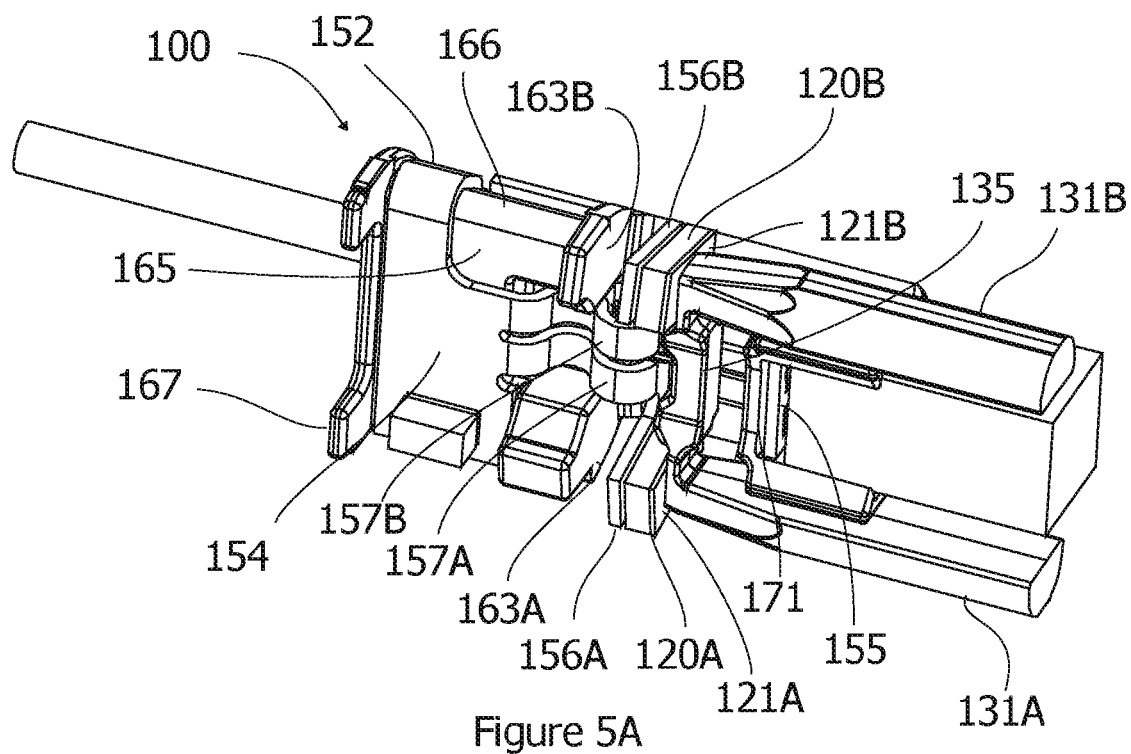

Inside the tip part 50, a vision assembly 100 is accommodated in the interior cavity 62, which is shown in detail in FIGS. 4A, 4B, and 5A. The vision assembly 100 comprises an imaging subassembly 110, two light sources 120A, 120B, a light guide part 130, an electrical circuit 150, and a frame component 160. In this disclosure, the suffixes A and B denote an element belonging to the first light source 120A and the second light source 120B, respectively. FIGS. 4A, 4B, and 5A illustrate the vision assembly 100 without the tip housing 60. A first subassembly 115 may comprise the imaging subassembly 110 and the frame component 160. A second subassembly 116 may comprise the two light sources 120A, 120B and the light guide part 130.

The imaging subassembly 110 is best seen in FIGS. 4A-5A and comprises an image sensor 111 viewing in an optical direction 112 through a lens barrel 113. The imaging subassembly 110 is arranged so that the optical direction passes through the window 65 of the tip housing 60, as best seen in FIGS. 5B-6B. The lens barrel 113 comprises several lenses enclosed in an opaque barrel typically provided by a polymer cylinder with an opaque, e.g. black, coating or paint extending circumferentially around on the outside of the cylinder. The lenses optimise the view of the image sensor 111 and the barrel forms an optical barrier, which reduces stray light entering the image sensor 111. In some variations, the lens barrel 113 may be omitted.

The two light sources 120A, 120B are best seen in FIGS. 4A-5A and are provided as a single phosphor-based light-emitting diode configured for emitting substantially white light. Each light source 120A, 120B comprises a single semiconductor die (not shown) for emitting light in an illumination direction 122A, 122B and surrounded by an epoxy-based cover with a planar exterior surface forming an illumination surface 121A, 121B. The illumination surfaces 121A, 121B are adhered to a light entry surface 132A, 132B of a respective light guide 131A, 131B by an adhesive. The light sources 120A, 120B are arranged proximally relative to the image sensor 111 to provide a more compact vision assembly 100. Alternatively, each light source could be the distal end of a respective optical fibre transporting light from an LED arranged in the handle of the endoscope.

The light guide part is best seen in FIG. 5B and comprises two light guides 131A, 131B, one for each light source 120A, 120B. The light guides 131A, 131B are spaced apart by a gap and extend in parallel along a respective straight longitudinal central centre line. Each light guide 131A, 131B has a respective light entry surface 132A, 132B, a light exit surface 133A, 133B and a circumferential surface 134A, 134B (best seen in FIGS. 4A-5A) extending from the light entry surface 132A, 132B to the light exit surface 133A, 133B around a respective longitudinal central centre line (coinciding with the respective illumination direction 122A, 122B shown in FIG. 5B). Each light guide 131A, 131B is configured for receiving light from its respective light source 120A, 120B through its light entry surface 131A, 131B and propagates the light through its light exit surface 133A, 133B and out through the window 65 of the tip housing 60. The light entry surfaces 132A, 132B and the light exit surfaces 133A, 133B are planar and parallel, and the circumferential surfaces 134A, 134B define a polymer-air interface between the light guide part 130 and the interior cavity 62. The light guide part 130 further includes a crossmember 135 extending transversely from a proximal end of the first light guide 131A to a proximal end of the second light guide 131B over the gap between the light guides 131A, 131B. The light guide part 130 is monolithically formed of a rigid and transparent polymer material with a refractive index that is higher than the refractive index of air. This ensures that the critical angle for total internal reflection of light incident on the circumferential surfaces 134A, 134B is increased and thus increases the ability of the light guides 131A, 131B to propagate light from the respective light entry surface 132A, 132B to the respective light exit surface 133A, 133B, thereby minimising light loss through the circumferential surfaces 134A, 134B.

The electrical circuit 150 is best seen in FIGS. 4A-5A and is configured for transmitting an image signal generated by the image sensor 111 indicative of the view in the optical direction 112 to the circuit (not shown) of the handle 20 via cables 159 for display on the monitor (which is shown in FIG. 2). The electrical circuit 150 is provided on a flexible circuit board (FPC) and comprises a main circuit portion 151, an imaging circuit portion 155, and two illumination circuit portions 156A, 156B. The imaging circuit portion 155 is in signal communication with the image sensor 111 of the imaging subassembly 110 and is connected to the main circuit portion 151.

The two illumination circuit portions 156A, 156B are respectively in electrical communication with and supply power to the light sources 120A, 120B and electrically connected to the main circuit portion via a respective bridge circuit portion 157A, 157B of the electrical circuit 150. The bridge circuit portions 157A, 157B are wave-shaped along the optical direction 112 and separated by a slit 158 of the electrical circuit 150.

Figure 7A:
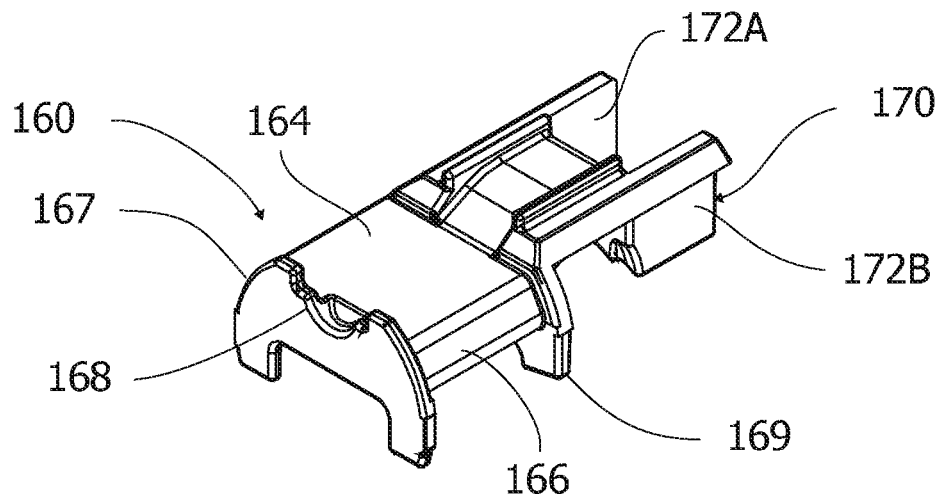
FIGS. 7A-7C are schematic perspective illustrations of a frame component of the vision assembly alone.
Figure 7B:
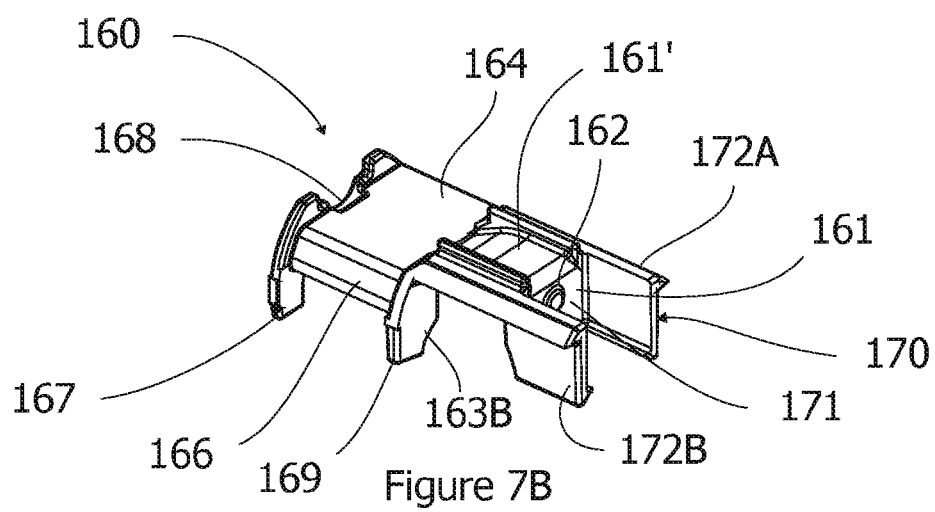
Figure 7C:
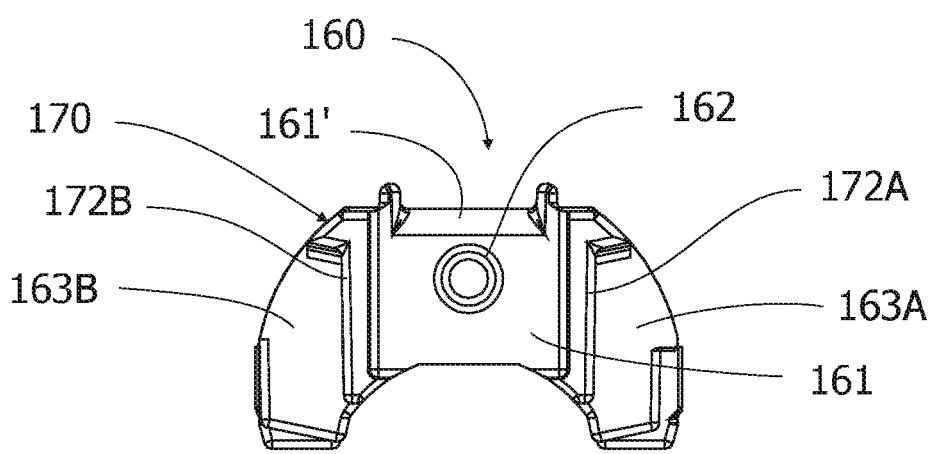

The frame component 160 supports and fixes the imaging subassembly 110, the two light sources 120A, 120B, and the electrical circuit 150 relative to each other, as best seen in FIGS. 4A-5A, while FIGS. 7A-7C show the frame component 160 individually.

The frame component 160 comprises a light shielding wall 170 of an opaque material that comprises an end wall 171 and two side walls 172A, 172B. The end wall 171 extends transversely to the optical direction 112 and between the image sensor 111 and the light sources 120A, 120B so as to shield the image sensor 111 from stray light emitted directly from the light sources 120A, 120B towards the image sensor 111. The two side walls 172A, 172B extend longitudinally and circumferentially relative to the optical direction 112 from the end wall 171. The two side walls 172A, 172B are positioned between the image sensor 111 and the light guides 131A, 131B, thus extending partially around the image sensor 111 and the lens barrel 113 so as to optically shield the imaging subassembly 110 from stray light escaping from the circumferential surfaces 134A, 134B of the light guides 131A, 131B towards the imaging subassembly 110.

A distal surface of the end wall 171 forms an imaging attachment surface 161 of the frame component 160. The imaging attachment surface 161 has a protrusion 162 (which is best seen in FIGS. 7B-7C). The protrusion 162 defines a well-defined contact point about which the imaging subassembly 110 can be oriented during assembly. Once the imaging subassembly 110, in particular the optical direction 112, has been aligned with respect to the frame component 160, an adhesive is applied in the gap between the imaging circuit portion 155 to the imaging attachment surface 161 surrounding the protrusion 162, thereby adhering and fixing the imaging subassembly 110 to the frame component 160.

The frame component 160 comprises two illumination attachment surfaces 163A, 163B, one for each light source. A gap between the illumination attachment surfaces 163, 163B and the illumination circuit portions 156A, 156B is filled with a cured adhesive. The gap allows an assembler to adjust the relative longitudinal positioning of the light guide part 130 and a first subassembly having the frame component 160 and the imaging subassembly 110, thus ensuring that the distal surfaces of these parts have the correct position to allow them to simultaneously contact the interior window surface 66 of the window 65.

The frame component 160 comprises a proximal collar 167 having an outer contour corresponding to and arranged with a gap to an interior surface of the circumferential wall 68 of the tip housing 60. The gap may be filled with a cured adhesive to fix the frame component 160 to the tip housing 60. The frame component 160 further comprises an intermediate collar 169 corresponding to the interior surface of the circumferential wall 68 of the tip housing 60. The light shielding wall 170 is arranged distally relative to the intermediate collar 169, while the proximal collar 167 is arranged proximally relative to the intermediate collar 169.

As best seen in FIGS. 7A-7C, the frame component 160 comprises an upper supporting surface 164, a lower supporting surface 165 arranged opposite of the upper supporting surface 164, and an intermediate connecting surface 166 connecting the upper supporting surface 164 with the lower supporting surface 165. The upper supporting surface 164, lower supporting surface 165, and intermediate connecting surface 166 are positioned between the proximal collar 167 and the intermediate collar 169. The upper supporting surface 164 and the lower supporting surface 165 may be provided by opposing walls disposed between the proximal collar 167 and the intermediate collar 169.

As best seen in FIGS. 4A-4B, an upper section 153 of the main circuit portion 151 is adhered to the upper supporting surface 164 of the frame component 160 (best seen in FIGS. 7A-7B) and is connected to the imaging circuit portion 155 via an imaging connecting circuit portion 155' supported by an imaging connecting surface 161' of the frame component 160. The imaging connecting surface 161' extends over and above the light sources 120A, 120B so that the imaging subassembly 110 is arranged distally relative to the light sources 120A, 120B. As best seen in FIG. 5A, the lower supporting surface 165 supports or fixes a lower section 154 of the main circuit portion 150 by adhesion. The intermediate connecting surface 166 supports a bend 152 of the main circuit 150 connecting the upper section 153 of the main circuit portion 150 with the lower section 154 of the main circuit portion 150.

A plurality of data and electrical cables 159 is soldered to the upper section 153 of the main circuit portion 151 and is configured for transmitting electrical signals between the electrical circuit 150 and a circuit (not shown) of the handle 20 of the endoscope 1. The proximal collar 167 comprise a cut-out 168 configured for accommodating the plurality of cables thus allowing the cables 159 to extend in parallel to the longitudinal axis 52, as best seen in FIGS. 4A and 4B.

Figure 6B:
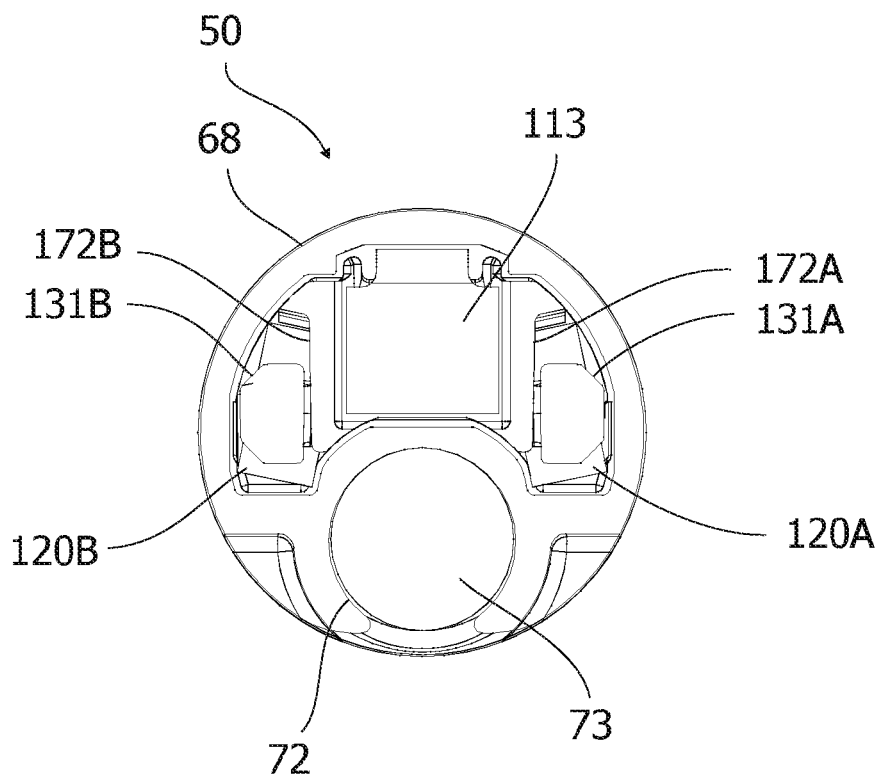
FIG. 6B is a schematic illustration of cross-section perpendicular the longitudinal axis of the endoscope tip part and through light guides of the vision assembly.

As best seen in FIG. 6A, the tip housing 60 comprises a distal working channel opening 72, a proximal working channel opening 71, and a working channel cavity 73 extending between the distal working channel opening 72 and the proximal working channel opening 71, thereby defining a tip working channel for forming part of the working channel of the endoscope 1. The working channel cavity 73 is separated from the interior cavity of the tip housing by a working channel wall 74. As best seen in FIG. 6B, the working channel cavity 73 has a substantially circular cross-section while a cross-section of the interior cavity 62 has a substantially crescent shape so that the circumference of the exterior housing surface 64 of the tip housing is substantially circular.

In the following, a method of assembling the above vision assembly 100 is described. The method comprises the steps of:
provoiding the following separate components or subassemblies: the above imaging subassembly 110, the two light sources 120A, 120B, the light guide part 130, the electrical circuit 150, and the frame component 160. The two light sources 120A, 120B are provided in electrical communication with their respective illumination circuit portions 156A, 156B, and the imaging subassembly 110 is provided with the image sensor 111 being in signal communication with the imaging circuit portion 155.

Figure 8A:
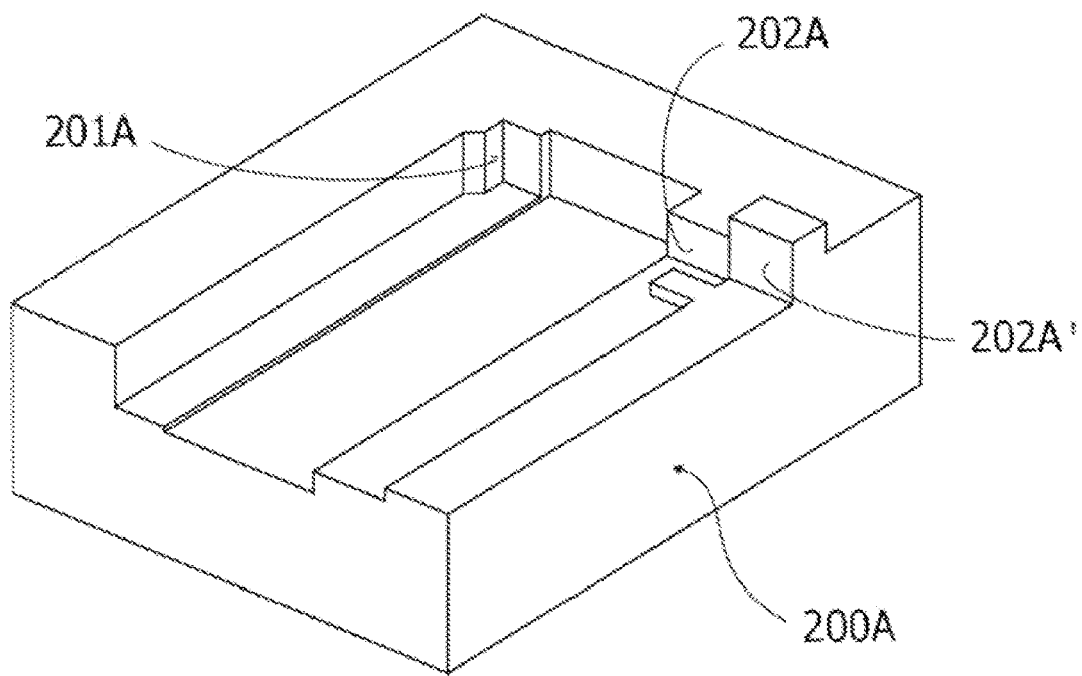
FIGS. 8A-8B are schematic perspective illustrations of a first alignment sequence involving a first jig.
Figure 8B:
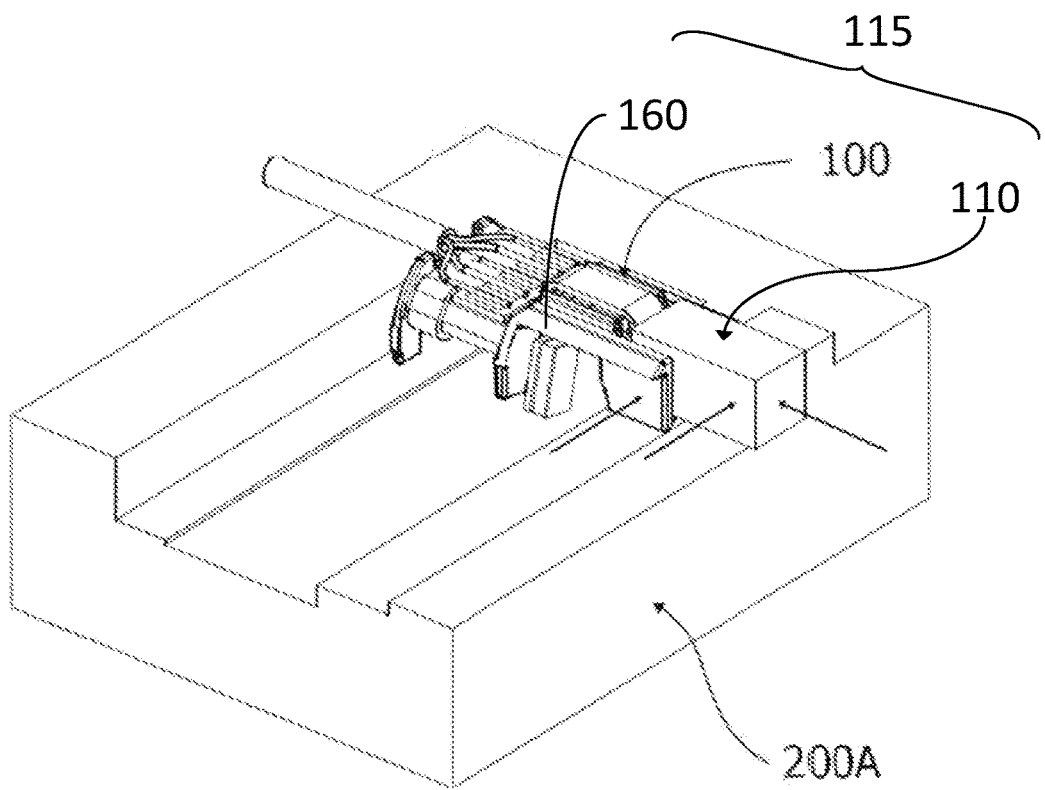

Then, a first alignment sequence is performed, as best illustrated in FIGS. 8A and 8B to obtain the first subassembly 115, the first alignment sequence comprises the steps of:
arranging the imaging subassembly 110 and the frame component 160 in a first jig 200A;
aligning the image sensor 111 with the frame component 160 by axially pushing on lens barrel 113 so that the proximal collar 167 of the frame component 160 contacts an axial stop 201A of the first jig 200A (see arrow in FIG. 8B);
aligning the image sensor 111 with the frame component 160 by transversely pushing on the lens barrel 113 and the frame component 160 so that the lens barrel 113 and the frame component 160 contact first transverse stops 202A, 202A' of the first jig 200A (see transverse arrows in FIG. 8B); and
adhering the imaging subassembly 110 to the frame component 160 by filling a gap between the imaging circuit portion 155 and the imaging attachment surface 161 of the frame component 160 (as best seen in FIG. 6A).

The imaging subassembly 110 and frame component 160 are now fixed to each other and form the first subassembly 115. A second alignment sequence is then performed, as best illustrated in FIGS. 9A-9D, to obtain the second subassembly 116, the second alignment sequence comprises the steps of:
placing the two light sources 120A, 120B and the light guide part 130 in a second jig 200B, which retains the light sources 120A, 120B in the desired position;
applying an adhesive to the illumination surfaces 121A, 121B of the light sources 120A, 120B;
placing the light entry surfaces 132A, 132B of the light guide part 130 in contact with the adhesive on the illumination surfaces 121A, 121B so that the second jig 200B retains the crossmember 135 of the light guide part 130;
aligning each of the two light sources 120A, 120B with the respective light guide 131A, 131B of the light guide part 130 by pushing the light exit surfaces 133A, 133B of the light guides 131A, 131B so that the illumination circuit portions contact second axial stops 201B of the second jig 200B (see arrows on FIG. 9C); and
adhering the illumination surface 121A, 121B of each of the two light sources 120A, 120B to a light entry surface 132A, 132B of the respective light guide 130A, 130B.

Figure 10A:
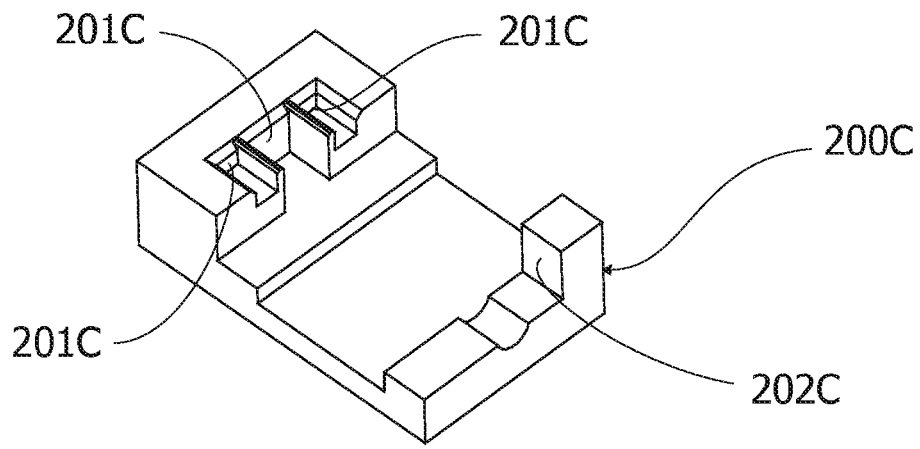
FIGS. 10A-10B are schematic perspective illustrations of a third alignment sequence involving a third jig.
Figure 10B:
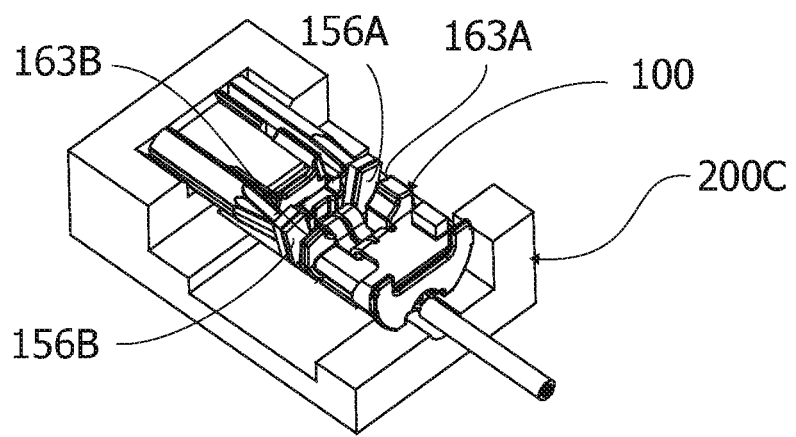

Thus, the two light sources 120A, 120B and the light guide part 130 form the second subassembly 116. A third alignment sequence is then performed, as best illustrated in FIGS. 10A-10C, to obtain the vision assembly 100, the third alignment sequence comprising the steps of:
arranging the first subassembly 115 and the second subassembly 116 in a third jig 200C;
aligning the first subassembly 115 and the second subassembly 116 by pushing the proximal collar 167 of the frame component 160 so that the light exit surfaces 133A, 133B and the lens barrel 113 contact against third axial stops 201C of the third jig 200C and by transversely pushing the proximal collar 167 so that the proximal collar 167 contracts a third transverse stop 202C of the third jig 200C; and
adhering the second subassembly 116 to the frame component 160 by filling respective gaps between the illumination circuit portions 156A, 156B and the illumination attachment surfaces 163A, 163B, as best seen in FIG. 10B.

The assembled vision assembly 100 is then inserted into a tip housing part (as previously disclosed) through the proximal opening 163 thereof so that the image sensor 111 views through the window 65 of the tip housing 60, and so that each light guide 131A, 131B of the light guide part 130 is arranged to propagate light received through its light entry surface 132A, 132B, through its light exit surface 133A, 133B and out through the window 65 of the tip housing 60. The proximal opening 63 of the tip housing 60 is then sealed by inserting a sealing element (not shown) and applying an adhesive so that the interior cavity is fluid-sealed, i.e. liquid- and airtight.

The following items are examples of various embodiments disclosed above:

Item 1. An endoscope tip part for an endoscope for visually inspecting inaccessible places, such as human body cavities, the endoscope tip part extending along a longitudinal axis from a proximal end thereof to a distal end thereof and comprising:
a tip housing extending circumferentially around and longitudinally along the longitudinal axis and defining an exterior surface of the endoscope tip part, the tip housing at least partially enclosing a fluid-sealed interior cavity, the tip housing including a window having an exterior window surface facing the exterior of the endoscope tip part and an interior window surface facing the interior cavity of the tip housing; and
a vision assembly accommodated in the interior cavity of the tip housing and including:
an imaging subassembly comprising an image sensor viewing in an optical direction,
one or more light sources each light source comprising an illumination surface from which the light source is configured to emit light in an illumination direction, and
a frame component being formed as a separate component, the frame component supporting and fixing the imaging subassembly and the one or more light sources relative to each other,
wherein the frame component comprises a light shielding wall being made of an opaque material and extending between the image sensor and the one or more light sources so as to at least partially shield the image sensor from light emitted from the one or more light sources.

Item 2. An endoscope tip part according to item 1, wherein the illumination surface of each of the one or more light sources is arranged proximally relative to the image sensor, and the light shielding wall comprises an end wall extending transversely to the optical direction, the end wall extending between the image sensor and the one or more light sources so as to optically shield a proximal side of the image sensor from the one or more light sources.

Item 3. An endoscope tip part according to any one of the previous items, wherein the vision assembly includes a light guide part comprising at least one light guide, each light guide having a light entry surface and a light exit surface and being configured for receiving light from at least one respective light source of the one or more light sources through its light entry surface and propagating said light through its light exit surface and out through the window of the tip housing.

Item 4. An endoscope tip part according to item 3, wherein the light shielding wall of the frame component comprises one or more side walls for each light guide extending along the respective light guide and being arranged between the light guide and the imaging subassembly.

Item 5. An endoscope tip part according to any one of items 3-4, wherein the light guide part is formed, preferably monolithically, as a separate component, and the illumination surface of each of the one or more light sources is attached, preferably adhered, to the light entry surface of its respective light guide.

Item 6. An endoscope tip part according to any one of the previous items, wherein the vision assembly includes an electrical circuit comprising an imaging circuit portion, the imaging circuit portion being in electrical communication with the image sensor, the electrical circuit being configured for transmitting an image signal generated by the image sensor indicative of the view in the optical direction.

Item 7. An endoscope tip part according to item 6, wherein the frame component comprises an imaging attachment surface, and wherein the imaging circuit portion is attached, preferably adhered, to the imaging attachment surface.

Item 8. An endoscope tip part according to any one of items 6-7, wherein the electric circuit comprises a main circuit portion being in electrical communication with the imaging circuit portion, the main circuit portion having a bend arranged around the frame component.

Item 9. An endoscope tip part according to any one of items 6-8, wherein the electrical circuit comprises one or more illumination circuit portions each being in electrical communication with a respective light source of the one or more light sources, each illumination circuit portion being electrically connected to the main circuit portion by a respective bridge circuit portion of the electrical circuit preferably having a wave-shaped extent along the optical direction.

Item 10. An endoscope tip part according to item 9, wherein the one or more light sources include at least a first light source and a second light source, and the electrical circuit has a slit separating the bridge circuit portions associated with the first and second light sources.

Item 11. An endoscope tip part according to any one of previous items, wherein the frame component comprises an illumination attachment surface for each light source, and wherein each light source, preferably via the illumination circuit portion, is attached, preferably adhered, to a respective illumination attachment surface.

Item 12. An endoscope for visually inspecting inaccessible places, such as human body cavities, comprising:
  a handle for gripping by an operator;
  an endoscope tip part according to any one of the previous items;
  an insertion cord for insertion into a patient, the insertion cord extending from the handle to the endoscope tip part;
  one or more cables running through the insertion cord and electrically connecting the endoscope tip part with the handle.

Item 13. An endoscope system for visually inspecting inaccessible places, such as human body cavities, the endoscope system comprising a monitor and an endoscope according to item 12 or an endoscope comprising an endoscope tip part according to any one of items 1-11, wherein the endoscope is connectable to the monitor, and the monitor is configured for displaying an image captured by the image sensor of the endoscope tip part.

Item 14. A method for assembling a vision assembly for an endoscope tip part, preferably according to any one of items 1-11, the endoscope tip part extending along a longitudinal axis from a proximal end thereof to a distal end thereof, the method comprising the steps of:
  providing:
    an imaging subassembly comprising an image sensor viewing in an optical direction;
    one or more light sources, such as a light-emitting diode or an optical fibre, each light source comprising an illumination surface from which the light source is configured to emit light in an illumination direction;
    a light guide part comprising at least one light guide, each light guide having a light entry surface and a light exit surface and being configured for receiving light from at least one respective light source of the one or more light sources through its light entry surface and propagating said light out through its light exit surface; and
    a frame component being formed as a separate component; and
  performing a first alignment sequence to obtain a first subassembly, the first alignment sequence comprises the steps of:
    aligning the image sensor with the frame component by axially pushing against an axial stop and by transversely pushing against a transverse stop; and
    fixing the imaging subassembly to the frame component; and
  performing a second alignment sequence to obtain a second subassembly, the second alignment sequence comprising the steps of:
    aligning each at least one light source of the one or more light sources with the respective light guide of the light guide part by pushing against an axial stop; and
    fixing each at least one light source of the one or more light sources to the light entry surface of the respective light guide; and
  performing a third alignment sequence to obtain the vision assembly, the third alignment sequence comprising the steps of:
    aligning the first subassembly and the second subassembly; and
    fixing the second subassembly to the frame component.

Item 15. A method according to item 14 for assembling the tip part for a medical device or preferably an endoscope for visually inspecting inaccessible places, such as human body cavities, the method further comprising the steps of:
  providing a tip housing extending circumferentially around and longitudinally along the longitudinal axis and defining an exterior surface of the endoscope tip part, the tip housing at least partially enclosing an interior cavity and having a proximal opening at the proximal end of the endoscope tip part providing access to the interior cavity, the tip housing including a window having an exterior window surface facing the exterior of the endoscope tip part and an interior window surface facing the interior cavity of the tip housing; and inserting the vision assembly through the proximal opening of the tip housing so that the image sensor views through the window of the tip housing, and so that each light guide of the light guide part is arranged to propagate light received through its light entry surface through its light exit surface and out through the window of the tip housing; and sealing the proximal opening of the tip housing so that the interior cavity is fluid-sealed.

| Reference numerals: | |
|---|---|
| 1 | endoscope |
| 11 | monitor |
| 12 | cable socket |
| 13 | monitor cable |
| 20 | handle |
| 21 | control lever |
| 22 | handle housing |
| 30 | insertion cord |
| 40 | bending section |
| 41 | proximal end |
| 42 | sleeve |
| 43 | segment |
| 44 | hinge |
| 50 | tip part |
| 51 | exterior surface |
| 52 | longitudinal axis |
| 60 | tip housing |
| 62 | interior cavity |
| 63 | proximal opening |
| 64 | exterior housing surface |
| 65 | window |
| 66 | interior window surface |
| 67 | exterior window surface |
| 68 | circumferential wall |
| 71 | proximal tip working channel opening |
| 72 | distal tip working channel opening |
| 73 | working channel cavity |
| 74 | working channel wall |
| 100 | vision assembly |
| 110 | imaging subassembly |
| 111 | image sensor |
| 112 | optical direction |
| 113 | lens barrel |
| 120 | light source |
| 121 | illumination surface |
| 122 | illumination direction |
| 130 | light guide part |
| 131 | light guide |
| 132 | light entry surface |
| 133 | light exit surface |
| 134 | circumferential surface |
| 135 | crossmember |
| 150 | electrical circuit |
| 151 | main circuit portion |
| 152 | bend |
| 153 | upper section |
| 154 | lower section |
| 155 | imaging circuit portion |
| 155' | imaging connecting circuit portion |
| 156 | illumination circuit portion |
| 157 | bridge circuit portion |
| 158 | slit |
| 159 | cable |
| 160 | frame component |
| 161 | imaging attachment surface |
| 161' | imaging connecting surface |
| 162 | protrusion |
| 163 | illumination attachment surface |
| 164 | upper supporting surface |

-continued

| Reference numerals: | |
|---|---|
| 165 | lower supporting surface |
| 166 | intermediate connecting surface |
| 167 | proximal collar |
| 168 | cable cut-out |
| 169 | intermediate collar |
| 170 | light shielding wall |
| 171 | end wall |
| 172 | side wall |
| 200 | jig |
| 201 | axial stop |
| 202 | traverse stop |

The invention claimed is:

1. An endoscope tip part for an endoscope, the endoscope tip part comprising:
a tip housing defining an interior cavity, the tip housing including a window having an exterior window surface facing an exterior of the endoscope tip part and an interior window surface facing the interior cavity; and
a vision assembly accommodated in the interior cavity and including:
an imaging subassembly comprising an image sensor with a view in an optical direction through the window;
a light source comprising an illumination surface to emit light in an illumination direction;
an electrical circuit connected to the light source and the image sensor; and
a frame component supporting, and fixing positions of, the imaging subassembly and the light source relative to each other, the frame component comprising a monolithic, one-piece, part including a light shielding wall, an intermediate collar, a proximal collar spaced apart from the intermediate collar, and an upper supporting surface extending between the proximal collar and the intermediate collar, the intermediate collar spaced apart from the light shielding wall, the light shielding wall made of an opaque material and including an end wall extending transversely to the optical direction and a side wall connected to and extending distally from the end wall, the imaging subassembly positioned distally of the end wall, and the light shielding wall extending between the image sensor and the light source so as to at least partially shield the image sensor from light emitted from the light source.

2. The endoscope tip part of claim 1, wherein the imaging subassembly comprises a lens barrel and a lens arranged in the lens barrel, and wherein the lens barrel is positioned distally of the image sensor.

3. The endoscope tip part of claim 1, wherein the illumination surface is arranged proximally relative to the image sensor.

4. The endoscope tip part of claim 3, wherein the vision assembly includes a light guide part comprising a light guide having a light entry surface and a light exit surface, wherein the light entry surface is aligned with the illumination surface to receive the light from the light source, and wherein the light guide propagates the light through the light exit surface and out through the window.

5. The endoscope tip part of claim 4, wherein the side wall extends between the imaging subassembly and the light guide.

6. The endoscope tip part of claim 5, wherein the illumination surface is attached to the light entry surface.

7. The endoscope tip part of claim 1, wherein the electrical circuit comprises an imaging circuit portion in electrical communication with the image sensor to transmit an image signal generated by the image sensor indicative of the view in the optical direction, wherein the frame component comprises an imaging attachment surface, and wherein the imaging circuit portion is attached to the imaging attachment surface.

8. The endoscope tip part of claim 7, wherein the imaging circuit portion is adhered to the imaging attachment surface.

9. The endoscope tip part of claim 8, wherein the electric circuit comprises a main circuit portion in electrical communication with the imaging circuit portion, the main circuit portion having a bend arranged around the frame component.

10. The endoscope tip part of claim 7, wherein the electrical circuit comprises a bridge circuit portion and an illumination circuit portion, the illumination circuit portion being in electrical communication with the light source and being electrically connected to the main circuit portion by the bridge circuit portion.

11. The endoscope tip part of claim 10, wherein the bridge circuit portion has a wave-shaped extent along the optical direction.

12. The endoscope tip part of claim 10, wherein the light source is a first light source and the bridge circuit portion is a first bridge circuit portion, the endoscope tip part further comprising a second light source and a second bridge circuit portion, and wherein the electrical circuit has a slit separating the first bridge circuit portion and the second bridge circuit portion.

13. The endoscope tip part of claim 12, wherein the frame component comprises a first illumination attachment surface and a second illumination attachment surface, and wherein the first light source is supported by the first illumination attachment surface and the second light source is supported by the second illumination attachment surface.

14. The endoscope tip part of claim 13, wherein the illumination circuit portion is a first illumination circuit portion affixed to the first illumination attachment surface and supporting the first light source, the endoscope tip part further comprising a second illumination circuit portion affixed to the second illumination attachment surface and supporting the second light source.

15. The endoscope tip part of claim 1, further comprising a light guide part comprising a crossmember extending transversely and a light guide extending distally from the crossmember, the light guide having a light entry surface and a light exit surface, the light entry surface longitudinally aligned with the illumination surface to receive the light from the light source, the light guide propagating the light through the light exit surface and out through the window, the end wall of the light shielding wall of the frame component positioned distally of the crossmember.

16. An endoscope comprising:
a handle;
the endoscope tip part according to claim 1;
an insertion cord extending from the handle to the endoscope tip part; and
one or more cables running through the insertion cord and electrically connecting the endoscope tip part with the handle.

17. An endoscope system comprising a monitor and the endoscope of claim 16, wherein the endoscope is connectable to the monitor, and wherein the monitor is configured to display an image captured by the image sensor.

18. An endoscope comprising:
a handle;
the endoscope tip part according to claim 1, the endoscope tip part further comprising a light guide part comprising a crossmember extending transversely and a light guide extending distally from the crossmember, the light guide having a light entry surface and a light exit surface, the light entry surface longitudinally aligned with the illumination surface to receive the light from the light source, the light guide propagating the light through the light exit surface and out through the window, the end wall of the light shielding wall of the frame component positioned distally of the crossmember;
an insertion cord extending from the handle to the endoscope tip part; and
one or more cables running through the insertion cord and electrically connecting the endoscope tip part with the handle.

* * * * *